(12) United States Patent
Olson et al.

(10) Patent No.: US 8,182,457 B2
(45) Date of Patent: May 22, 2012

(54) GARMENT HAVING AN APPARENT ELASTIC BAND

(75) Inventors: Christopher Peter Olson, Neenah, WI (US); Raymond Jeffrey May, Norcross, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2417 days.

(21) Appl. No.: 09/855,196

(22) Filed: May 14, 2001

(65) Prior Publication Data

US 2004/0019343 A1 Jan. 29, 2004

Related U.S. Application Data

(60) Provisional application No. 60/204,197, filed on May 15, 2000.

(51) Int. Cl.
*A61F 13/15* (2006.01)
(52) U.S. Cl. ......... 604/385.24; 604/385.25; 604/385.26; 604/385.27; 604/385.01
(58) Field of Classification Search ............. 604/385.27, 604/385.01, 385.24, 385.26, 385.3, 385.23, 604/385.25
See application file for complete search history.

(56) References Cited

U.S. PATENT DOCUMENTS

| | | | |
|---|---|---|---|
| 2,206,761 A | 7/1940 | Bergstein | 93/6 |
| 2,266,761 A | 12/1941 | Jackson, Jr. et al. | 154/46 |
| 2,357,392 A | 9/1944 | Francis, Jr. | 18/47.5 |
| 2,464,301 A | 3/1949 | Francis, Jr. | 154/46 |
| 2,483,405 A | 10/1949 | Francis, Jr. | 154/54 |
| 2,957,512 A | 10/1960 | Wade et al. | 154/33.05 |
| 2,957,852 A | 10/1960 | Frankenburg et al. | 260/75 |
| 3,186,893 A | 6/1965 | Mercer | 161/60 |
| 3,338,992 A | 8/1967 | Kinney | 264/24 |
| 3,341,394 A | 9/1967 | Kinney | 161/72 |
| 3,371,668 A | 3/1968 | Johnson | 128/290 |
| 3,391,048 A | 7/1968 | Dyer et al. | 161/58 |
| 3,439,085 A | 4/1969 | Hartmann | 264/210 |
| 3,449,187 A | 6/1969 | Bobkowicz | 156/161 |
| 3,468,748 A | 9/1969 | Bassett | 161/122 |
| 3,489,148 A | 1/1970 | Duncan et al. | |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,575,782 A | 4/1971 | Hansen | 161/141 |

(Continued)

FOREIGN PATENT DOCUMENTS

CA 2165486 6/1996

(Continued)

OTHER PUBLICATIONS

Cellular Materials to Composites, *Encyclopedia of Polymer Science and Engineering*, vol. 3, pp. 299-300, (1985), John Wiley & Sons.

*Primary Examiner* — Jacqueline F. Stephens
(74) *Attorney, Agent, or Firm* — Armstrong Teasdale LLP

(57) ABSTRACT

A disposable garment includes a chassis defining one or more openings for the legs, arms, waist or the like on a wearer. An apparent elastic band is located in the vicinity of at least one of the openings. The apparent elastic band looks and functions like an elastic band, but is not an elastic band, and is less expensive to implement than an elastic band.

36 Claims, 13 Drawing Sheets

U.S. PATENT DOCUMENTS

| | | | | |
|---|---|---|---|---|
| 3,616,129 A | 10/1971 | Sager | | 161/57 |
| 3,629,047 A | 12/1971 | Davison | | 161/57 |
| 3,669,823 A | 6/1972 | Wood | | 161/141 |
| 3,673,026 A | 6/1972 | Brown | | 156/164 |
| 3,676,242 A | 7/1972 | Prentice | | 156/62.4 |
| 3,689,342 A | 9/1972 | Vogt et al. | | 156/167 |
| 3,692,618 A | 9/1972 | Dorschner et al. | | 161/72 |
| 3,752,613 A | 8/1973 | Vogt et al. | | 425/80 |
| 3,773,590 A | 11/1973 | Morgan | | 156/244 |
| 3,802,817 A | 4/1974 | Matsuki et al. | | 425/66 |
| 3,806,289 A | 4/1974 | Schwarz | | 425/72 |
| 3,836,416 A | 9/1974 | Ropiequet | | 161/2 |
| 3,838,692 A | 10/1974 | Levesque | | |
| 3,849,241 A | 11/1974 | Butin et al. | | 161/169 |
| 3,857,144 A | 12/1974 | Bustin | | |
| 3,860,003 A | 1/1975 | Buell | | |
| 3,890,184 A | 6/1975 | Morgan | | 156/244 |
| 3,904,465 A | 9/1975 | Haase et al. | | |
| 3,912,567 A | 10/1975 | Schwartz | | 156/167 |
| 3,917,448 A | 11/1975 | Wood | | 8/125 |
| 3,932,328 A | 1/1976 | Korpman | | |
| 3,949,128 A | 4/1976 | Ostermeier | | |
| 3,949,130 A | 4/1976 | Sabee et al. | | 428/192 |
| 3,973,063 A | 8/1976 | Clayton | | |
| 3,978,185 A | 8/1976 | Buntin et al. | | 264/93 |
| 3,979,050 A | 9/1976 | Cilia | | |
| 4,013,816 A | 3/1977 | Sabee et al. | | 428/192 |
| 4,028,292 A | 6/1977 | Korpman | | |
| 4,038,346 A | 7/1977 | Feeney | | |
| 4,080,348 A | 3/1978 | Korpman | | |
| 4,090,385 A | 5/1978 | Packard | | 72/191 |
| 4,107,364 A | 8/1978 | Sisson | | 428/196 |
| 4,148,676 A | 4/1979 | Paquette et al. | | 156/181 |
| 4,209,563 A | 6/1980 | Sisson | | 428/288 |
| 4,211,807 A | 7/1980 | Yazawa et al. | | 428/109 |
| 4,239,578 A | 12/1980 | Gore | | 156/361 |
| 4,241,123 A | 12/1980 | Shih | | 428/105 |
| 4,248,652 A | 2/1981 | Civardi et al. | | |
| 4,259,220 A | 3/1981 | Bunnelle et al. | | 260/27 BB |
| 4,285,998 A | 8/1981 | Thibodeau | | |
| 4,300,562 A | 11/1981 | Pieniak | | |
| 4,302,495 A | 11/1981 | Marra | | 428/110 |
| 4,303,571 A | 12/1981 | Jansen et al. | | 260/33.6 AQ |
| 4,304,234 A | 12/1981 | Hartmann | | 128/287 |
| 4,310,594 A | 1/1982 | Yamazaki et al. | | 428/296 |
| 4,319,572 A | 3/1982 | Widlund et al. | | 128/284 |
| 4,323,534 A | 4/1982 | DesMarais | | 264/176 R |
| 4,333,782 A | 6/1982 | Pieniak | | 156/164 |
| 4,340,558 A | 7/1982 | Hendrickson | | |
| 4,340,563 A | 7/1982 | Appel et al. | | 264/518 |
| 4,375,446 A | 3/1983 | Fujii et al. | | 264/518 |
| 4,402,688 A | 9/1983 | Julemont | | |
| 4,405,397 A | 9/1983 | Teed | | 156/164 |
| 4,413,623 A | 11/1983 | Pieniak | | 604/365 |
| 4,417,935 A | 11/1983 | Spencer | | 156/80 |
| 4,418,123 A | 11/1983 | Bunnelle et al. | | 428/517 |
| 4,438,167 A | 3/1984 | Schwarz | | |
| 4,440,819 A | 4/1984 | Rosser et al. | | 428/107 |
| 4,490,427 A | 12/1984 | Grant et al. | | 428/107 |
| 4,496,417 A | 1/1985 | Haake et al. | | 156/361 |
| 4,500,316 A | 2/1985 | Damico | | |
| 4,507,163 A | 3/1985 | Menard | | 156/164 |
| 4,522,863 A | 6/1985 | Keck et al. | | |
| 4,525,407 A | 6/1985 | Ness | | 428/138 |
| 4,543,099 A | 9/1985 | Bunnelle et al. | | 604/385 A |
| 4,548,859 A | 10/1985 | Kline et al. | | 428/251 |
| 4,552,795 A | 11/1985 | Hansen et al. | | 428/110 |
| 4,555,811 A | 12/1985 | Shimalla | | 2/51 |
| 4,572,752 A | 2/1986 | Jensen et al. | | 156/64 |
| 4,586,199 A | 5/1986 | Birring | | 2/401 |
| D284,036 S | 6/1986 | Birring | | D2/10 |
| 4,606,964 A | 8/1986 | Wideman | | 428/152 |
| 4,618,384 A | 10/1986 | Sabee | | |
| 4,626,305 A | 12/1986 | Suzuki et al. | | 156/164 |
| 4,636,419 A | 1/1987 | Madsen et al. | | 428/131 |
| 4,640,859 A | 2/1987 | Hansen et al. | | 428/105 |
| 4,644,045 A | 2/1987 | Fowells | | |
| 4,652,487 A | 3/1987 | Morman | | 428/138 |
| 4,656,081 A | 4/1987 | Ando et al. | | 428/233 |
| 4,657,793 A | 4/1987 | Fisher | | 428/36 |
| 4,657,802 A | 4/1987 | Morman | | 428/152 |
| 4,661,389 A | 4/1987 | Mudge et al. | | |
| 4,663,220 A | 5/1987 | Wisneski et al. | | 428/221 |
| 4,666,542 A | 5/1987 | De Jonckheere | | 156/164 |
| 4,675,068 A | 6/1987 | Lundmark | | 156/495 |
| 4,683,877 A | 8/1987 | Ersfeld et al. | | 128/90 |
| 4,687,477 A | 8/1987 | Suzuki et al. | | 604/385 A |
| 4,692,368 A | 9/1987 | Taylor et al. | | 428/137 |
| 4,692,371 A | 9/1987 | Morman et al. | | 428/224 |
| 4,704,116 A | 11/1987 | Enloe | | 604/385 A |
| 4,718,901 A | 1/1988 | Singheimer | | 604/385 A |
| 4,719,261 A | 1/1988 | Bunnelle et al. | | 525/97 |
| 4,720,415 A | 1/1988 | Vander Wielen et al. | | 428/152 |
| 4,725,468 A | 2/1988 | McIntyre | | 428/40 |
| 4,726,874 A | 2/1988 | VanVliet | | 156/495 |
| 4,734,311 A | 3/1988 | Sokolowski | | 428/152 |
| 4,734,320 A | 3/1988 | Ohira et al. | | 428/231 |
| 4,734,447 A | 3/1988 | Hattori et al. | | |
| 4,735,673 A | 4/1988 | Piron | | 156/496 |
| 4,756,942 A | 7/1988 | Aichele | | 428/102 |
| 4,761,198 A | 8/1988 | Salerno | | 156/334 |
| 4,762,582 A | 8/1988 | de Jonckheere | | 156/164 |
| 4,775,579 A | 10/1988 | Hagy et al. | | 428/284 |
| 4,777,080 A | 10/1988 | Harris, Jr. et al. | | 428/212 |
| 4,789,699 A | 12/1988 | Kieffer et al. | | 524/271 |
| 4,798,603 A | 1/1989 | Meyer et al. | | |
| 4,801,345 A | 1/1989 | Dussaud et al. | | 156/164 |
| 4,801,482 A | 1/1989 | Goggans et al. | | 428/68 |
| 4,803,117 A | 2/1989 | Daponte | | 428/228 |
| 4,804,577 A | 2/1989 | Hazelton et al. | | 428/224 |
| 4,816,094 A | 3/1989 | Pomplun et al. | | |
| 4,818,597 A | 4/1989 | DaPonte et al. | | |
| 4,826,415 A | 5/1989 | Mende | | 425/722 |
| 4,837,715 A | 6/1989 | Ungpiyakul et al. | | |
| 4,842,666 A | 6/1989 | Werenicz | | 156/161 |
| 4,854,985 A | 8/1989 | Soderlund et al. | | 156/85 |
| 4,854,989 A | 8/1989 | Singheimer | | 156/161 |
| 4,863,779 A | 9/1989 | Daponte | | 428/152 |
| 4,867,735 A | 9/1989 | Wogelius | | |
| 4,874,447 A | 10/1989 | Hazelton et al. | | 156/167 |
| 4,883,482 A | 11/1989 | Gandrez et al. | | 604/385.2 |
| 4,883,549 A | 11/1989 | Frost et al. | | 156/161 |
| 4,891,258 A | 1/1990 | Fahrenkrug | | 428/138 |
| 4,892,536 A | 1/1990 | DesMarais et al. | | 604/385.2 |
| 4,892,903 A | 1/1990 | Himes | | 524/488 |
| 4,900,619 A | 2/1990 | Ostrowski et al. | | 428/284 |
| 4,906,507 A | 3/1990 | Grynaeus et al. | | 428/113 |
| 4,908,247 A | 3/1990 | Baird et al. | | 428/34.9 |
| 4,908,253 A | 3/1990 | Rasmussen | | |
| 4,910,064 A | 3/1990 | Sabee | | 428/113 |
| 4,917,696 A | 4/1990 | De Jonckheere | | 604/385.2 |
| 4,917,746 A | 4/1990 | Kons et al. | | 156/164 |
| 4,929,492 A | 5/1990 | Carey, Jr. et al. | | 428/198 |
| 4,935,021 A | 6/1990 | Huffman et al. | | |
| 4,938,753 A | 7/1990 | Van Gompel et al. | | |
| 4,938,757 A | 7/1990 | Van Gompel et al. | | |
| 4,938,821 A | 7/1990 | Soderlund et al. | | 156/85 |
| 4,940,464 A | 7/1990 | Van Gompel et al. | | |
| 4,965,122 A | 10/1990 | Morman | | 428/225 |
| 4,968,313 A | 11/1990 | Sabee | | 604/385.2 |
| 4,970,259 A | 11/1990 | Mitchell et al. | | 524/505 |
| 4,977,011 A | 12/1990 | Smith | | 428/152 |
| 4,984,584 A | 1/1991 | Hansen et al. | | 128/898 |
| 4,994,508 A | 2/1991 | Shiraki et al. | | |
| 4,995,928 A | 2/1991 | Sabee | | 156/164 |
| 4,998,929 A | 3/1991 | Björksund et al. | | 604/385.2 |
| 5,000,806 A | 3/1991 | Merkatoris et al. | | 156/161 |
| 5,002,815 A | 3/1991 | Yamanaka et al. | | 428/109 |
| 5,005,215 A | 4/1991 | McIlquham | | |
| 5,013,785 A | 5/1991 | Mizui | | |
| 5,028,646 A | 7/1991 | Miller et al. | | |
| 5,034,008 A | 7/1991 | Breitkopf | | |
| 5,045,133 A | 9/1991 | DaPonte et al. | | |
| 5,046,272 A | 9/1991 | Vogt et al. | | |
| 5,060,349 A | 10/1991 | Walton et al. | | 26/18.6 |
| 5,073,436 A | 12/1991 | Antonacci et al. | | 428/219 |
| 5,093,422 A | 3/1992 | Himes | | 525/98 |

| | | | | | | | |
|---|---|---|---|---|---|---|---|
| 5,100,435 | A | 3/1992 | Onwumere ............... 8/115.55 | 5,472,775 | A | 12/1995 | Obijeski et al. ............... 428/220 |
| 5,104,116 | A | 4/1992 | Pohjola | 5,476,458 | A | 12/1995 | Glaug et al. |
| 5,108,820 | A | 4/1992 | Kaneko et al. | 5,476,563 | A | 12/1995 | Nakata ........................ 156/167 |
| 5,112,889 | A | 5/1992 | Miller et al. | 5,484,645 | A | 1/1996 | Lickfield et al. ............... 428/198 |
| 5,114,087 | A | 5/1992 | Fisher et al. ............... 242/42 | 5,486,166 | A | 1/1996 | Bishop et al. |
| 5,116,662 | A | 5/1992 | Morman | 5,490,846 | A | 2/1996 | Ellis et al. |
| 5,147,487 | A | 9/1992 | Nomura et al. ............... 156/164 | 5,496,298 | A | 3/1996 | Kuepper et al. |
| 5,151,092 | A | 9/1992 | Buell et al. | 5,498,468 | A | 3/1996 | Blaney ........................ 428/198 |
| 5,163,932 | A | 11/1992 | Nomura et al. | 5,500,075 | A | 3/1996 | Herrmann ................... 156/494 |
| D331,627 | S | 12/1992 | Igaue et al. ............... D24/126 | 5,501,679 | A | 3/1996 | Krueger et al. |
| 5,169,706 | A | 12/1992 | Collier, IV et al. ............ 428/152 | 5,503,919 | A | 4/1996 | Litchholt et al. |
| 5,169,712 | A | 12/1992 | Tapp ........................ 428/315.5 | 5,509,915 | A | 4/1996 | Hanson et al. |
| 5,176,668 | A | 1/1993 | Bernardin | 5,514,470 | A | 5/1996 | Haffner et al. ............... 428/246 |
| 5,176,672 | A | 1/1993 | Bruemmer et al. | 5,516,476 | A | 5/1996 | Haggard et al. ............... 264/211 |
| 5,186,779 | A | 2/1993 | Tubbs ........................ 156/161 | 5,523,146 | A | 6/1996 | Bodford et al. ............... 428/198 |
| 5,192,606 | A | 3/1993 | Proxmire et al. | 5,527,300 | A | 6/1996 | Sauer |
| 5,198,281 | A | 3/1993 | Muzzy et al. ............... 428/102 | 5,531,850 | A | 7/1996 | Herrmann ................... 156/161 |
| 5,200,246 | A | 4/1993 | Sabee ........................ 428/109 | 5,534,330 | A | 7/1996 | Groshens ................... 428/198 |
| 5,204,429 | A | 4/1993 | Kaminsky et al. ............ 526/308 | 5,540,796 | A | 7/1996 | Fries |
| D335,707 | S | 5/1993 | Igaue et al. ............... D24/126 | 5,540,976 | A | 7/1996 | Shawver et al. ............... 428/198 |
| 5,209,801 | A | 5/1993 | Smith ........................ 156/161 | 5,543,206 | A | 8/1996 | Austin et al. |
| 5,219,633 | A | 6/1993 | Sabee ........................ 428/109 | 5,545,158 | A | 8/1996 | Jessup ........................ 604/385.2 |
| 5,224,405 | A | 7/1993 | Pohjola | 5,545,285 | A | 8/1996 | Johnson ................... 156/496 |
| 5,226,992 | A | 7/1993 | Morman ................... 156/62.4 | 5,549,964 | A | 8/1996 | Shohji et al. ............... 428/224 |
| 5,229,191 | A | 7/1993 | Austin ........................ 428/198 | 5,561,858 | A | 10/1996 | Poirier |
| 5,232,777 | A | 8/1993 | Sipinen et al. ............... 428/364 | 5,569,232 | A | 10/1996 | Roe et al. ................... 604/385.2 |
| 5,236,430 | A | 8/1993 | Bridges ........................ 604/396 | 5,575,783 | A | 11/1996 | Clear et al. ................... 604/385.1 |
| 5,236,770 | A | 8/1993 | Assent et al. ............... 428/198 | 5,576,090 | A | 11/1996 | Suzuki ........................ 428/152 |
| 5,238,733 | A | 8/1993 | Joseph et al. ............... 428/284 | 5,582,606 | A | 12/1996 | Bruemmer et al. |
| 5,246,433 | A | 9/1993 | Hasse et al. ............... 604/396 | 5,582,668 | A | 12/1996 | Kling ........................ 156/161 |
| D340,283 | S | 10/1993 | Igaue et al. ............... D24/126 | 5,591,152 | A | 1/1997 | Buell et al. ................... 604/385.2 |
| 5,252,170 | A | 10/1993 | Schaupp | 5,591,792 | A | 1/1997 | Hattori et al. |
| 5,259,902 | A | 11/1993 | Muckenfuhs ............... 156/164 | 5,595,618 | A | 1/1997 | Fries et al. |
| 5,260,126 | A | 11/1993 | Collier, IV et al. ............ 428/288 | 5,597,430 | A | 1/1997 | Rasche ........................ 156/161 |
| 5,272,236 | A | 12/1993 | Lai et al. ................... 526/348.5 | 5,612,118 | A | 3/1997 | Schleinz et al. |
| 5,278,272 | A | 1/1994 | Lai et al. ................... 526/348.5 | 5,614,276 | A | 3/1997 | Petsetakis |
| 5,288,791 | A | 2/1994 | Collier, IV et al. ............ 524/505 | 5,620,780 | A | 4/1997 | Krueger et al. |
| 5,290,842 | A | 3/1994 | Sasaki et al. | 5,624,740 | A | 4/1997 | Nakata ........................ 428/204 |
| 5,296,080 | A | 3/1994 | Merkatoris et al. ............ 156/496 | 5,626,573 | A | 5/1997 | Igaue et al. ................... 604/385.1 |
| 5,304,599 | A | 4/1994 | Himes ........................ 525/98 | 5,628,856 | A | 5/1997 | Dobrin et al. ............... 156/244.18 |
| 5,308,345 | A | 5/1994 | Herrin ........................ 604/385.2 | 5,645,672 | A | 7/1997 | Dobrin ........................ 156/244.18 |
| 5,312,500 | A | 5/1994 | Kurihara et al. ............... 156/62.4 | 5,652,041 | A | 7/1997 | Buerger et al. ............... 428/198 |
| 5,324,580 | A | 6/1994 | Allan et al. ................... 428/284 | 5,660,664 | A | 8/1997 | Herrmann ................... 156/161 |
| 5,332,613 | A | 7/1994 | Taylor et al. ............... 428/152 | 5,663,228 | A | 9/1997 | Sasaki et al. |
| 5,334,437 | A | 8/1994 | Zafiroglu ........................ 428/219 | 5,669,897 | A | 9/1997 | Lavon et al. ................... 604/385.2 |
| 5,334,446 | A | 8/1994 | Quantrille et al. ............ 428/284 | 5,674,216 | A | 10/1997 | Buell et al. |
| 5,336,545 | A | 8/1994 | Morman ........................ 428/152 | 5,680,653 | A | 10/1997 | Mathis et al. |
| 5,336,552 | A | 8/1994 | Strack et al. | 5,681,302 | A | 10/1997 | Melbye et al. ............... 604/373 |
| 5,342,341 | A | 8/1994 | Igaue et al. | 5,681,645 | A * | 10/1997 | Strack et al. ................... 428/196 |
| 5,342,469 | A | 8/1994 | Bodford et al. ............... 156/244.22 | 5,683,787 | A | 11/1997 | Boich et al. ................... 428/198 |
| 5,360,854 | A | 11/1994 | Bozich, Jr. ................... 524/274 | 5,690,626 | A | 11/1997 | Suzuki et al. ............... 604/385.2 |
| 5,364,382 | A | 11/1994 | Latimer et al. | 5,691,034 | A | 11/1997 | Krueger et al. |
| 5,366,793 | A | 11/1994 | Fitts, Jr. et al. ............ 428/198 | 5,693,038 | A | 12/1997 | Suzuki et al. ............... 604/385.2 |
| 5,376,198 | A | 12/1994 | Fahrenkrug et al. ............ 156/164 | 5,695,849 | A | 12/1997 | Shawver et al. ............... 428/131 |
| 5,376,430 | A | 12/1994 | Swenson et al. | 5,702,378 | A | 12/1997 | Widlund et al. |
| 5,382,400 | A | 1/1995 | Pike et al. | 5,707,709 | A | 1/1998 | Blake |
| 5,385,775 | A | 1/1995 | Wright ........................ 428/284 | 5,709,921 | A | 1/1998 | Shawver ........................ 428/152 |
| H1420 | H | 2/1995 | Richardson | 5,720,838 | A | 2/1998 | Nakata ........................ 156/167 |
| 5,389,173 | A | 2/1995 | Merkatoris et al. ............ 156/164 | 5,733,635 | A | 3/1998 | Terakawa et al. ............... 428/198 |
| 5,393,599 | A | 2/1995 | Quantrille et al. ............ 428/284 | 5,733,822 | A | 3/1998 | Gessner et al. ............... 442/35 |
| 5,399,219 | A | 3/1995 | Roessler et al. | 5,735,839 | A | 4/1998 | Kawaguchi et al. ........ 604/385.2 |
| 5,405,682 | A | 4/1995 | Shawver et al. ............... 428/221 | 5,736,219 | A | 4/1998 | Suehr et al. ................... 428/113 |
| 5,407,507 | A | 4/1995 | Ball ........................ 156/163 | 5,746,731 | A | 5/1998 | Hisada ........................ 604/385.2 |
| 5,411,618 | A | 5/1995 | Jocewicz, Jr. ............... 156/164 | 5,749,865 | A | 5/1998 | Yamamoto et al. ........ 604/385.2 |
| 5,413,654 | A | 5/1995 | Igaue et al. ............... 156/161 | 5,749,866 | A | 5/1998 | Roe et al. ................... 604/385.2 |
| 5,413,849 | A | 5/1995 | Austin et al. ............... 428/293 | 5,766,389 | A | 6/1998 | Brandon et al. |
| 5,415,644 | A | 5/1995 | Enloe | 5,766,737 | A | 6/1998 | Willey et al. ............... 428/198 |
| 5,415,649 | A | 5/1995 | Watanabe et al. ............ 604/385.2 | 5,769,838 | A | 6/1998 | Buell et al. ................... 604/396 |
| 5,415,925 | A | 5/1995 | Austin et al. ............... 428/287 | 5,769,993 | A | 6/1998 | Baldauf ........................ 156/164 |
| 5,422,172 | A | 6/1995 | Wu | 5,772,649 | A | 6/1998 | Siudzinski ................... 604/386 |
| 5,425,987 | A | 6/1995 | Shawver et al. ............... 428/284 | 5,773,373 | A | 6/1998 | Wynne et al. ............... 442/260 |
| 5,429,629 | A | 7/1995 | Latimer et al. | 5,773,374 | A | 6/1998 | Wood et al. ............... 442/328 |
| 5,429,694 | A | 7/1995 | Herrmann ................... 156/164 | 5,788,804 | A | 8/1998 | Hörsting ........................ 156/440 |
| 5,431,644 | A | 7/1995 | Sipinen et al. ............... 604/385.2 | 5,789,065 | A | 8/1998 | Haffner et al. ............... 428/152 |
| 5,431,991 | A | 7/1995 | Quantrille et al. ............ 428/109 | 5,789,328 | A | 8/1998 | Kurihara et al. ............... 442/387 |
| 5,447,462 | A | 9/1995 | Smith et al. ................... 450/122 | 5,789,474 | A | 8/1998 | Lu et al. |
| 5,447,508 | A | 9/1995 | Numano et al. ............ 604/385.2 | 5,800,903 | A | 9/1998 | Wood et al. |
| 5,449,353 | A | 9/1995 | Watanabe et al. ............ 604/385.2 | 5,804,021 | A | 9/1998 | Abuto et al. |
| 5,464,401 | A | 11/1995 | Hasse et al. ............... 604/385.1 | 5,804,286 | A | 9/1998 | Quantrille et al. |

| | | | | | |
|---|---|---|---|---|---|
| 5,814,176 | A | 9/1998 | Proulx | ................... | 156/167 |
| 5,817,087 | A | 10/1998 | Takabayashi et al. | ..... | 604/385.2 |
| 5,818,719 | A | 10/1998 | Brandon et al. | | |
| 5,830,203 | A | 11/1998 | Suzuki et al. | ........ | 604/385.2 |
| 5,834,089 | A | 11/1998 | Jones et al. | ............. | 428/97 |
| 5,836,931 | A | 11/1998 | Toyoda et al. | ......... | 604/385.2 |
| 5,836,932 | A | 11/1998 | Buell et al. | ............. | 604/396 |
| 5,840,412 | A | 11/1998 | Wood et al. | | |
| 5,840,633 | A | 11/1998 | Kurihara et al. | | |
| 5,846,232 | A | 12/1998 | Serbiak et al. | | |
| 5,849,001 | A | 12/1998 | Torimae et al. | | |
| 5,856,387 | A | 1/1999 | Sasaki et al. | | |
| 5,860,945 | A | 1/1999 | Cramer et al. | | |
| 5,865,933 | A | 2/1999 | Morin et al. | | |
| 5,876,392 | A | 3/1999 | Hisada | ............... | 604/385.2 |
| 5,879,776 | A | 3/1999 | Nakata | .................. | 428/92 |
| 5,882,573 | A | 3/1999 | Kwok et al. | ........... | 264/510 |
| 5,883,028 | A | 3/1999 | Morman et al. | | |
| 5,885,656 | A | 3/1999 | Goldwasser | | |
| 5,885,686 | A | 3/1999 | Cederblad et al. | ........... | 428/107 |
| 5,895,382 | A | 4/1999 | Popp et al. | | |
| 5,897,546 | A | 4/1999 | Kido et al. | ............ | 604/391 |
| 5,899,895 | A | 5/1999 | Robles et al. | ........... | 604/385.2 |
| 5,902,540 | A | 5/1999 | Kwok | ................... | 264/555 |
| 5,904,298 | A | 5/1999 | Kwok et al. | ........... | 239/135 |
| 5,906,637 | A | 5/1999 | Davis et al. | | |
| 5,916,206 | A | 6/1999 | Otsubo et al. | ........... | 604/385.2 |
| 5,921,973 | A | 7/1999 | Newkirk et al. | | |
| 5,930,139 | A | 7/1999 | Chapdelaine et al. | | |
| 5,931,581 | A | 8/1999 | Garberg et al. | | |
| 5,932,039 | A | 8/1999 | Popp et al. | | |
| 5,941,865 | A | 8/1999 | Otsubo et al. | ........... | 604/385.2 |
| D414,262 | S | 9/1999 | Ashton et al. | .............. | D24/126 |
| 5,952,252 | A | 9/1999 | Shawver et al. | ........... | 442/407 |
| 5,964,970 | A | 10/1999 | Woolwine et al. | ............ | 156/64 |
| 5,964,973 | A | 10/1999 | Heath et al. | | |
| 5,990,377 | A | 11/1999 | Chen et al. | | |
| 5,993,433 | A | 11/1999 | St. Louis et al. | | |
| 5,997,521 | A | 12/1999 | Robles et al. | ........... | 604/385.2 |
| 6,004,306 | A | 12/1999 | Robles et al. | ........... | 604/385.1 |
| 6,009,558 | A | 1/2000 | Rosch et al. | | |
| 6,033,502 | A | 3/2000 | Coenen et al. | ................ | 156/64 |
| 6,045,543 | A | 4/2000 | Pozniak et al. | ........... | 604/385.1 |
| 6,048,326 | A | 4/2000 | Davis et al. | | |
| 6,057,024 | A | 5/2000 | Mleziva et al. | ............ | 428/114 |
| 6,066,369 | A | 5/2000 | Schulz et al. | | |
| 6,087,550 | A | 7/2000 | Anderson-Fischer et al. | | |
| 6,090,234 | A | 7/2000 | Barone et al. | | |
| 6,092,002 | A | 7/2000 | Kastman et al. | | |
| 6,093,663 | A | 7/2000 | Ouellette et al. | | |
| 6,096,668 | A | 8/2000 | Abuto et al. | | |
| 6,121,510 | A | 9/2000 | Sauer | | |
| 6,123,694 | A | 9/2000 | Pieniak et al. | | |
| 6,132,410 | A | 10/2000 | Van Gompel et al. | | |
| 6,152,904 | A | 11/2000 | Matthews et al. | | |
| 6,169,848 | B1 | 1/2001 | Henry | | |
| 6,183,587 | B1 | 2/2001 | McFall et al. | | |
| 6,183,847 | B1 | 2/2001 | Goldwasser | | |
| 6,197,012 | B1 | 3/2001 | Mishima et al. | | |
| 6,214,476 | B1 | 4/2001 | Ikeda et al. | | |
| 6,217,690 | B1 | 4/2001 | Rajala et al. | | |
| 6,221,483 | B1 | 4/2001 | Hilston et al. | | |
| 6,231,557 | B1 | 5/2001 | Krautkramer et al. | | |
| 6,238,379 | B1 | 5/2001 | Keuhn, Jr. et al. | | |
| 6,245,050 | B1 | 6/2001 | Odorzynski et al. | | |
| 6,245,168 | B1 | 6/2001 | Coenen et al. | | |
| 6,248,097 | B1 | 6/2001 | Beitz et al. | | |
| 6,260,211 | B1 | 7/2001 | Rajala et al. | | |
| 6,279,807 | B1 | 8/2001 | Crowley et al. | | |
| 6,290,979 | B1 | 9/2001 | Roe et al. | | |
| 6,310,164 | B1 | 10/2001 | Morizono et al. | | |
| 6,316,013 | B1 | 11/2001 | Paul et al. | | |
| 6,316,687 | B1 | 11/2001 | Davis et al. | | |
| 6,316,688 | B1 | 11/2001 | Hammons et al. | | |
| 6,320,096 | B1 | 11/2001 | Inoui et al. | | |
| 6,323,389 | B1 | 11/2001 | Thomas et al. | | |
| 6,329,459 | B1 | 12/2001 | Kang et al. | | |
| 6,364,863 | B1 | 4/2002 | Yamamoto et al. | | |
| 6,365,659 | B1 | 4/2002 | Aoyama et al. | | |
| 6,417,121 | B1 | 7/2002 | Newkirk et al. | | |
| 6,475,600 | B1 | 11/2002 | Morman et al. | | |
| 6,478,786 | B1 * | 11/2002 | Glaug et al. | ............. | 604/385.27 |
| 6,537,935 | B1 | 3/2003 | Seth et al. | | |
| 6,562,167 | B2 | 5/2003 | Coenen et al. | | |
| 2002/0002021 | A1 | 1/2002 | May et al. | | |
| 2002/0009940 | A1 | 1/2002 | May et al. | | |
| 2002/0019616 | A1 | 2/2002 | Thomas | | |
| 2002/0104608 | A1 | 8/2002 | Welch et al. | | |
| 2002/0138063 | A1 | 9/2002 | Kuen et al. | | |
| 2002/0164465 | A1 | 11/2002 | Curro et al. | | |

FOREIGN PATENT DOCUMENTS

| | | |
|---|---|---|
| DE | 34 23 644 A1 | 1/1986 |
| DE | 37 34 963 A1 | 4/1988 |
| EP | 0 155 636 A2 | 9/1985 |
| EP | 0 172 037 A1 | 2/1986 |
| EP | 0 217 032 A2 | 4/1987 |
| EP | 239 080 A2 | 9/1987 |
| EP | 380 781 A2 | 8/1990 |
| EP | 456 885 B1 | 11/1991 |
| EP | 547 497 A2 | 6/1993 |
| EP | 570 980 A1 | 11/1993 |
| EP | 604 731 A1 | 7/1994 |
| EP | 617 939 A2 | 10/1994 |
| EP | 0 396 800 B1 | 8/1995 |
| EP | 0 688 550 A1 | 12/1995 |
| EP | 0 689 815 A1 | 1/1996 |
| EP | 743 052 A2 | 11/1996 |
| EP | 753 292 A2 | 1/1997 |
| EP | 713 546 B1 | 3/1997 |
| EP | 761 193 A2 | 3/1997 |
| EP | 761 194 A2 | 3/1997 |
| EP | 763 353 A2 | 3/1997 |
| EP | 787 474 A1 | 8/1997 |
| EP | 806 196 A2 | 11/1997 |
| EP | 814 189 A1 | 12/1997 |
| EP | 582 569 B1 | 6/1998 |
| EP | 0 873 738 A2 | 10/1998 |
| EP | 0 901 780 A1 | 3/1999 |
| EP | 1 013 251 A1 | 6/2000 |
| EP | 547497 B2 | 7/2000 |
| EP | 0 888 101 B1 | 5/2001 |
| GB | 2 267 024 | 11/1993 |
| GB | 2 244 422 B | 3/1994 |
| GB | 2 253 131 B | 10/1994 |
| GB | 2 250 921 B | 6/1995 |
| GB | 2 268 389 B | 7/1996 |
| IL | 92891 | 2/1992 |
| JP | 3-67646 | 3/1991 |
| JP | 10075978 | 3/1998 |
| JP | 10165438 | 6/1998 |
| WO | 90/03464 | 4/1990 |
| WO | WO 91/07277 | 5/1991 |
| WO | 92/16371 | 10/1992 |
| WO | 93/15247 | 8/1993 |
| WO | 93/17648 | 9/1993 |
| WO | 94/09736 | 5/1994 |
| WO | 95/03443 | 2/1995 |
| WO | 95/04182 | 2/1995 |
| WO | 95/16562 | 6/1995 |
| WO | WO 95/16425 | 6/1995 |
| WO | 95/34264 | 12/1995 |
| WO | 96/13989 | 5/1996 |
| WO | 96/23466 | 8/1996 |
| WO | 96/35402 | 11/1996 |
| WO | WO 97/17046 | 5/1997 |
| WO | 98/14156 | 4/1998 |
| WO | WO 98/49988 | 11/1998 |
| WO | 98/55062 | 12/1998 |
| WO | 99/17926 | 4/1999 |
| WO | WO 99/24519 | 5/1999 |
| WO | WO 99/47590 | 9/1999 |
| WO | 99/60969 | 12/1999 |
| WO | 99/60970 | 12/1999 |
| WO | 99/60971 | 12/1999 |
| WO | WO 00/10500 | 3/2000 |
| WO | WO 00/29199 | 5/2000 |
| WO | 00/37003 | 6/2000 |

| | | |
|---|---|---|
| WO | 00/37005 | 6/2000 |
| WO | WO 00/37723 | 6/2000 |
| WO | WO 00/59429 | 10/2000 |
| WO | WO 01/00053 A1 | 1/2001 |
| WO | WO 01/32116 A1 | 5/2001 |
| WO | WO 01/49907 A2 | 7/2001 |
| WO | WO 01/87214 A1 | 11/2001 |
| WO | WO 02/34184 A1 | 5/2002 |
| WO | WO 02/060690 A2 | 8/2002 |

\* cited by examiner

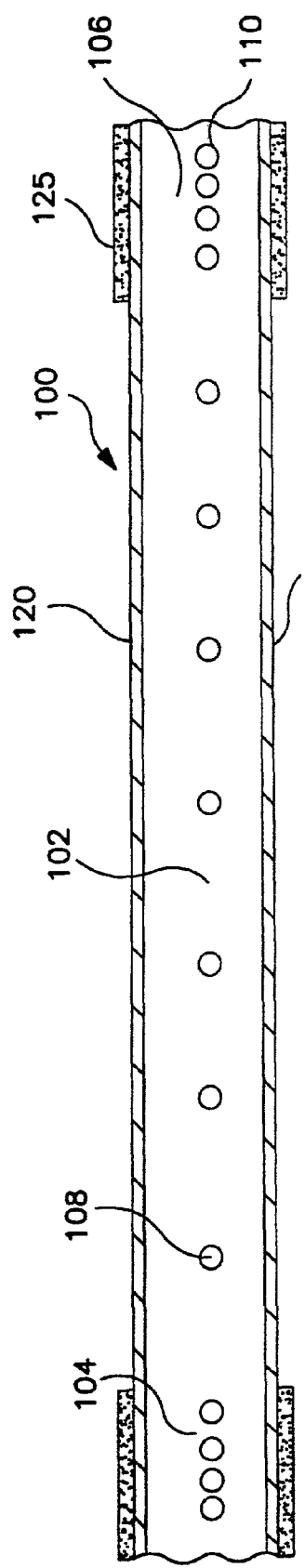
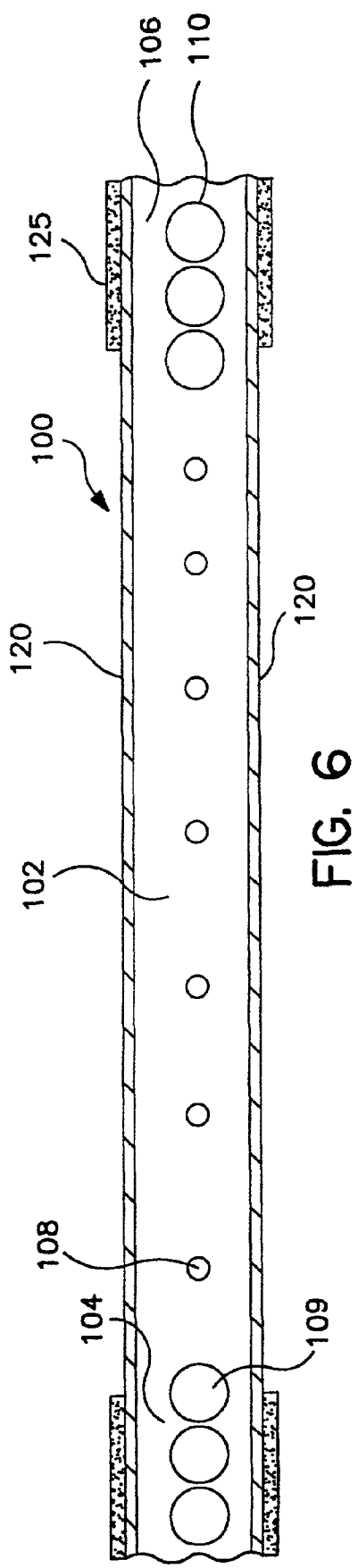
FIG. 5
FIG. 6

GARMENT HAVING AN APPARENT ELASTIC BAND

CROSS REFERENCE TO RELATED APPLICATION

The application claims the benefit to U.S. Provisional Application No. 60/204,197, filed 15 May 2000.

FIELD OF THE INVENTION

This invention relates to a garment having at least one apparent elastic band which looks and functions like a conventional elastic band, but is not a conventional elastic band.

BACKGROUND OF THE INVENTION

Garments, including pant-like absorbent garments, medical garments, and other products, are commonly made with an elastic band adjacent to at least one of the garment openings. A pant-like garment, for instance, may have an elastic band adjacent to the waist opening, each of the two leg openings, or all three of the openings. The elastic band adjacent to the waist opening holds the garment in place, and prevents it from falling off of the wearer. The elastic bands adjacent to the leg openings help to seal the garment against the wearer's legs, thereby preventing or reducing leakage of waste materials from inside the garment.

In conventional garments, the primary material for the garment is manufactured and assembled separately from the elastic bands. Following their separate manufacture, the elastic bands are attached to the primary material at some stage during manufacture of the garment by sewing, ultrasonic welding, thermal bonding, adhesive bonding, or the like. In the resulting product, the user can often see the elastic band as a distinct entity attached to the garment. If there is no visible evidence of an elastic band, the product may be perceived as inelastic (i.e., as not having an elastic band), or may be perceived as having inadequate elastic properties.

Because of competition, there is an incentive to reduce both material and manufacturing costs associated with garments, without sacrificing performance and quality. One way is to eliminate the use of a separately manufactured elastic band. However, because the use of visible, distinct elastic bands has gained widespread consumer acceptance, there is incentive to at least maintain the perception of a visibly distinct elastic band where elastic properties exist.

SUMMARY OF THE INVENTION

The present invention is directed to a garment having an apparent elastic band adjacent to one or more garment openings in a main body portion or "chassis." The garment has targeted elastic properties at the opening achieved without the use of a separately manufactured, separately attached elastic band, and is thus easier to manufacture than a conventional garment having one or more elastic bands at the garment opening or openings. The garment is modified at the opening or openings to create the visible perception of a discrete elastic band, even though no such band is present.

In one embodiment, the garment is manufactured from a primary material having targeted elastic properties in the region of the garment opening or openings. The primary material has a substantially homogeneous appearance, and carries no visible indication of a discrete elastic band. Yet the primary material has different elastic properties at different regions, and exhibits greater elastic tension in the vicinity of the one or more garment openings. In order to create the visible perception of an elastic band, the garment is modified by adding a relatively inexpensive, stretchable but inelastic band of material adjacent to the one or more garment openings. For instance, a band of a stretchable nonwoven material (e.g., a neck-stretched spunbond material) may be affixed to the primary garment material in the region of the openings. Alternatively, a band of colored pigment may be added to the garment at the targeted elastic region, to create the visible perception of a distinct, separately formed elastic band. Alternatively, both of these techniques may be combined by adding the colored pigment to the stretchable but inelastic band of material, and attaching the latter to the primary garment material.

With the foregoing in mind, it is a feature and advantage of the invention to provide a garment having an apparent elastic band in the vicinity of one or more garment openings, while eliminating the separate manufacture and attachment of an elastic band.

It is also a feature and advantage of the invention to provide various techniques for providing a garment with an apparent elastic band.

These and other features and advantages of the invention will become further apparent from the following detailed description of the presently preferred embodiments, read in conjunction with the drawings.

BRIEF DESCRIPTION OF THE DRAWINGS

FIGS. 5-8 illustrate representative targeted elastic laminate ("TEL") materials useful for making the garments having apparent elastic bands;

DEFINITIONS

Figure 1:
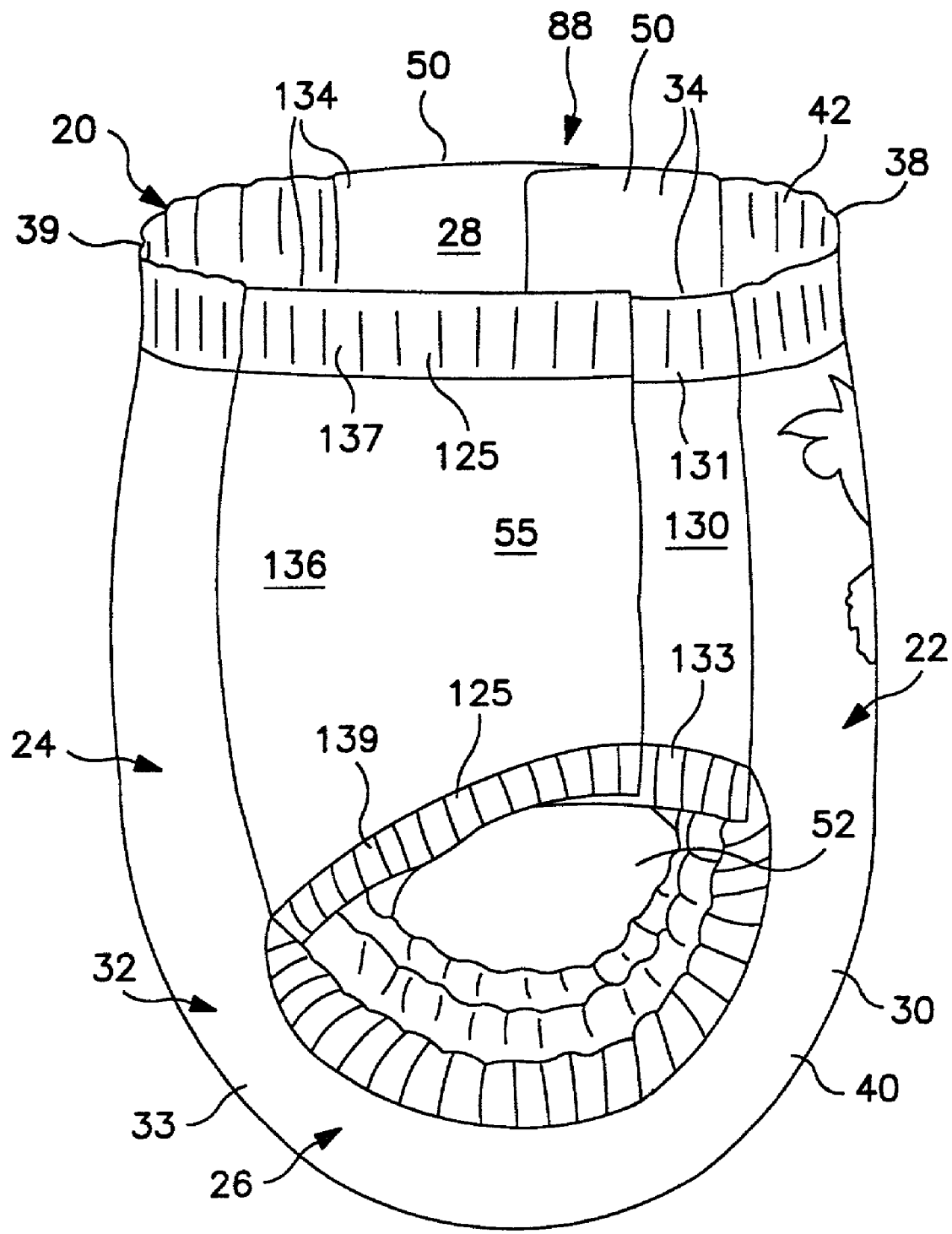
FIG. 1 illustrates a perspective view of a pant-like absorbent garment in accordance with the invention, having apparent elastic bands around the garment openings.

The term "elastic band" refers to a discrete elongated element having elastic properties. The term "discrete elongated element" refers to a long, relatively narrow element that is separately manufactured and then attached to an underlying material, and does not include elongated regions having elastic properties that may be part of the underlying material as made. The terms "elastic" and "elastomeric" are used interchangeably to mean a material that is generally capable of recovering its shape after deformation when the deforming force is removed. Specifically, as used herein, elastic or elastomeric is meant to be that property of any material which upon application of a biasing force, permits that material to be stretchable to a stretched biased length which is at least about 50 percent greater than its relaxed unbiased length, and that will cause the material to recover at least 40 percent of its elongation upon release of the stretching force. A hypothetical example which would satisfy this definition of an elastomeric material would be a one (1) inch sample of a material which is elongatable to at least 1.50 inches and which, upon being elongated to 1.50 inches and released, will recover to a length of not more than 1.30 inches. Many elastic materials may be stretched by much more than 50 percent of their relaxed length, and many of these will recover to substantially their original relaxed length upon release of the stretching force.

The term "inelastic" refers to materials that are not elastic.

The term "apparent elastic band" is an element, and/or part of an underlying material, that looks like an elastic band and behaves like an elastic band, but is not an elastic band (i.e., is not a discrete elongated element having elastic properties). This term includes a material having targeted elastic regions which are not initially apparent to the naked eye, which has been modified to visually distinguish the targeted elastic regions from the remaining regions of the material. An apparent elastic band may include, as one component, a stretchable material overlaying all or part of the waist region or leg cuff/hem areas of a garment, that looks like a waistband or leg band. The stretchable material is extendible so it does not significantly inhibit the stretch of the elastic panels or cover to which it is attached. The stretchable material has no significant retraction properties of its own. It can be attached to underlying elastic materials that provide elastic retraction to provide fit, comfort and ease of use in the garment. The apparent elastic band would include both the stretchable material (which is in the form of a band) and an outer edge of the underlying elastic material which is not formed as a band. The apparent elastic band can be attached outside or inside or both outside and inside the garment as when it is folded over like a hem or bounded edge.

The term "targeted elastic regions" refers to isolated, often relatively narrow bands or regions in a single composite material or layer, which have greater elastic tension than adjacent or surrounding regions.

The term "targeted elastic material" ("TEM") refers to a single elastic material or laminate having targeted elastic regions. TEM's include only materials or laminates which are made in a single manufacturing process, and which are capable of exhibiting targeted elastic properties without requiring an added elastic band or layer in the targeted elastic region. TEM's do not include materials having elasticized regions achieved through separate manufacture of an elastic band, and subsequent connection of the elastic band to the underlying material. TEM's include materials having apparent elastic bands as defined above.

The term "targeted elastic laminate" or "TEL" refers to an elastic laminate which behaves as a TEM. The TEL suitably includes at least one elastic nonwoven filament web, in which different zones of different elastic tension exist across a width of the web when the laminate is stretched in a longitudinal direction perpendicular to the width. The different zones may, but do not necessarily, have different elongations at break, or recoveries. What is important is that the different zones exhibit different levels of retractive force when the laminate is uniformly stretched by a selected amount. The elastic nonwoven filament web is laminated to at least one other layer, whereby the laminate exhibits different levels of elastic tension in zones corresponding to the high and low tension zones in the nonwoven filament web.

The term "targeted elastic stretch-bonded laminate" or "TE SBL" refers to a TEL which is formed by stretching the elastic nonwoven filament web having the zones of different elastic tension, maintaining the stretched condition of the elastic nonwoven filament web when the other layer is bonded to it, and relaxing the TEL after bonding.

The term "vertical filament stretch-bonded laminate" or "VF SBL" refers to a stretch-bonded laminate made using a continuous vertical filament process, as described herein.

The term "continuous filament stretch-bonded laminate" or "CF SBL" refers to a stretch-bonded laminate made using a continuous horizontal filament process, as described herein.

The term "elastic tension" refers to the amount of force per unit width required to stretch an elastic material (or a selected zone thereof) to a given percent elongation.

The term "low tension zone" or "lower tension zone" refers to a zone or region in a stretch-bonded laminate material having one or more filaments with low elastic tension characteristics relative to the filament(s) of a high tension zone, when a stretching or biasing force is applied to the stretch-bonded laminate material. Thus, when a biasing force is applied to the material, the low tension zone will stretch more easily than the high tension zone. At 50% elongation of the fabric, the high tension zone may exhibit elastic tension at least 10% greater, suitably at least 50% greater, desirably about 100-800% greater, or alternatively about 150-300% greater than the low tension zone.

The term "high tension zone" or "higher tension zone" refers to a zone or region in a stretch-bonded laminate material having one or more filaments with high elastic tension characteristics relative to the filament(s) of a low tension zone, when a stretching or biasing force is applied to the stretch-bonded laminate material. Thus, when a biasing force is applied to the material, the high tension zone will stretch less easily than the low tension zone. Thus, high tension zones have a higher tension than low tension zones. The terms "high tension zone" and "low tension zone" are relative, and the material may have multiple zones of different tensions.

The term "nonwoven fabric or web" means a web having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and carded (thermally bonded or hydraulically entangled) web processes. The term also includes films that have been cut into narrow strips, perforated or otherwise treated to allow air to pass through. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "microfibers" means small diameter fibers having an average diameter not greater than about 75 microns, for example, having an average diameter of from about 1 micron to about 50 microns, or more particularly, having an average diameter of from about 1 micron to about 30 microns.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface. Meltblown fibers used in the invention are suitably substantially continuous.

The term "polymer" generally includes but is not limited to, homopolymers, copolymers, including block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "substantially continuous filaments or fibers" refers to filaments or fibers prepared by extrusion from a spinnerette, including without limitation spunbonded and meltblown fibers, which are not cut from their original length prior to being formed into a nonwoven web or fabric. Substantially continuous filaments or fibers may have lengths ranging from greater than about 15 cm to more than one meter; and up to the length of the nonwoven web or fabric being formed. The definition of "substantially continuous filaments or fibers" includes those which are not cut prior to being formed into a nonwoven web or fabric, but which are later cut when the nonwoven web or fabric is cut.

The term "staple filaments or fibers" means filaments or fibers which are natural or which are cut from a manufactured filament prior to forming into a web, and which have a length ranging from about 0.1-15 cm, more commonly about 0.2-7 cm.

The term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

The term "thermoplastic" is meant to describe a material that softens when exposed to heat and which substantially returns to its original condition when cooled to room temperature.

The term "recover" or "retract" relates to a contraction of a stretched material upon termination of a biasing force following stretching of the material by application of the biasing force.

The term "garment" includes personal care garments, protective garments, and the like. The term "disposable garment" includes garments which are typically disposed of after 1-5 uses.

The term "personal care garment" includes diapers, training pants, swim wear, absorbent underpants, adult incontinence products, feminine hygiene products, and the like.

The term "protective garment" includes protective (i.e., medical and/or industrial) gowns, caps, gloves, drapes, face masks, and the like.

The term "in the vicinity of garment openings" refers to a region of the garment within about two inches, suitably within about one inch, of a garment opening, such as a leg or waist opening. An elastic band or zone is said to be "in the vicinity of a garment opening" if any portion of the elastic band or zone is within two inches, suitably within one inch of the garment opening.

The term "series" refers to a set including one or more elements.

DETAILED DESCRIPTION OF THE PRESENTLY PREFERRED EMBODIMENTS

The principles of this invention can be applied to a wide variety of garments, including disposable garments, having a targeted elastic zone in the vicinity of at least one garment opening. Examples include diapers, training pants, certain feminine hygiene products, adult incontinence products, other personal care or medical garments, and the like. For ease of explanation, the following description is in terms of a child training pant having a targeted elastic material, in this case a targeted elastic laminate, used for the side panels.

Referring to FIG. 1, a disposable absorbent garment 20, such as a child training pant, includes an absorbent chassis 32 and a fastening system 88. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 3 and 4, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39. The chassis 32 defines waist opening 50 and two opposing leg openings 52.

Figure 3:
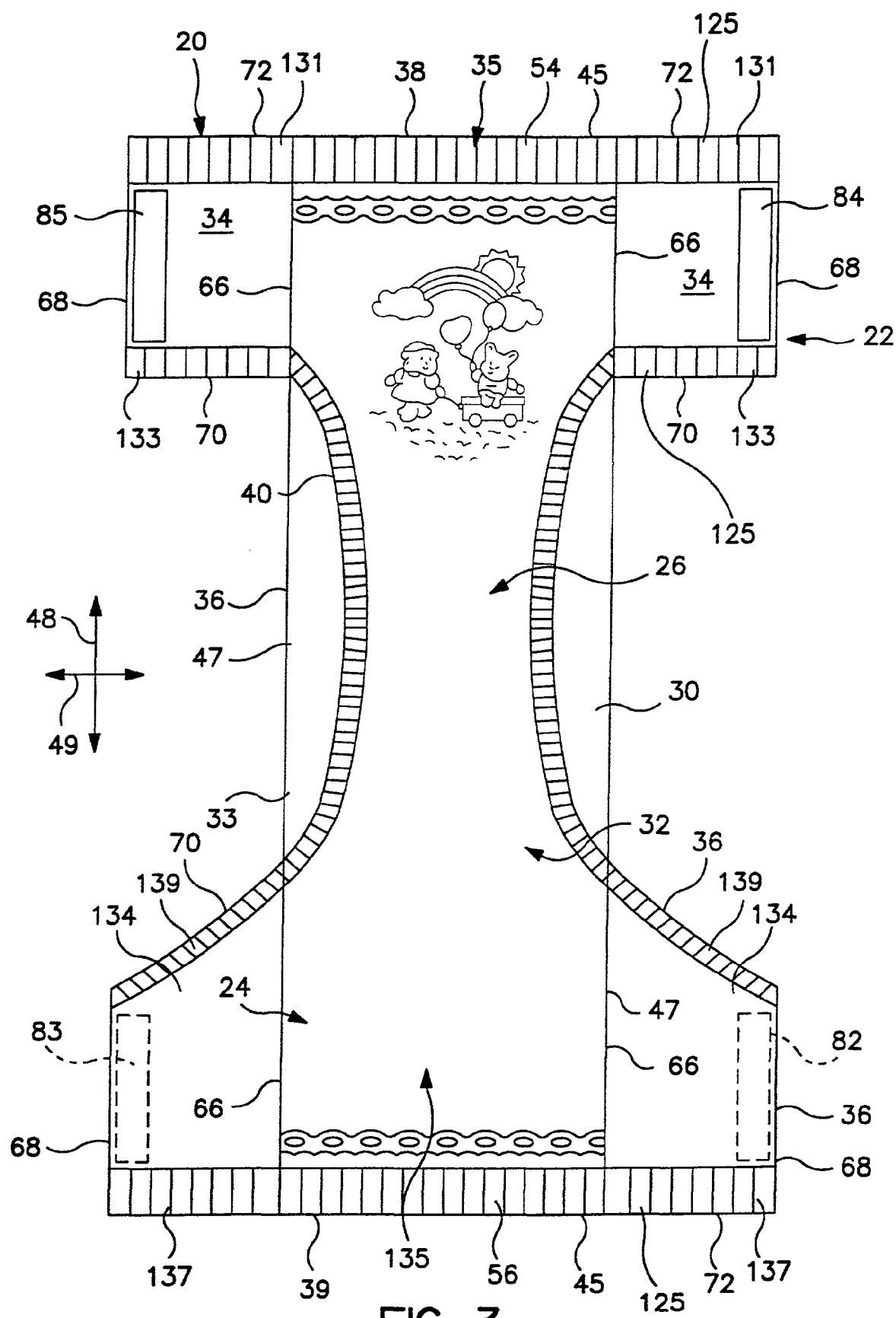
FIG. 3 is a plan view of the garment shown in FIG. 1, showing the side facing away from the wearer.
Figure 4:
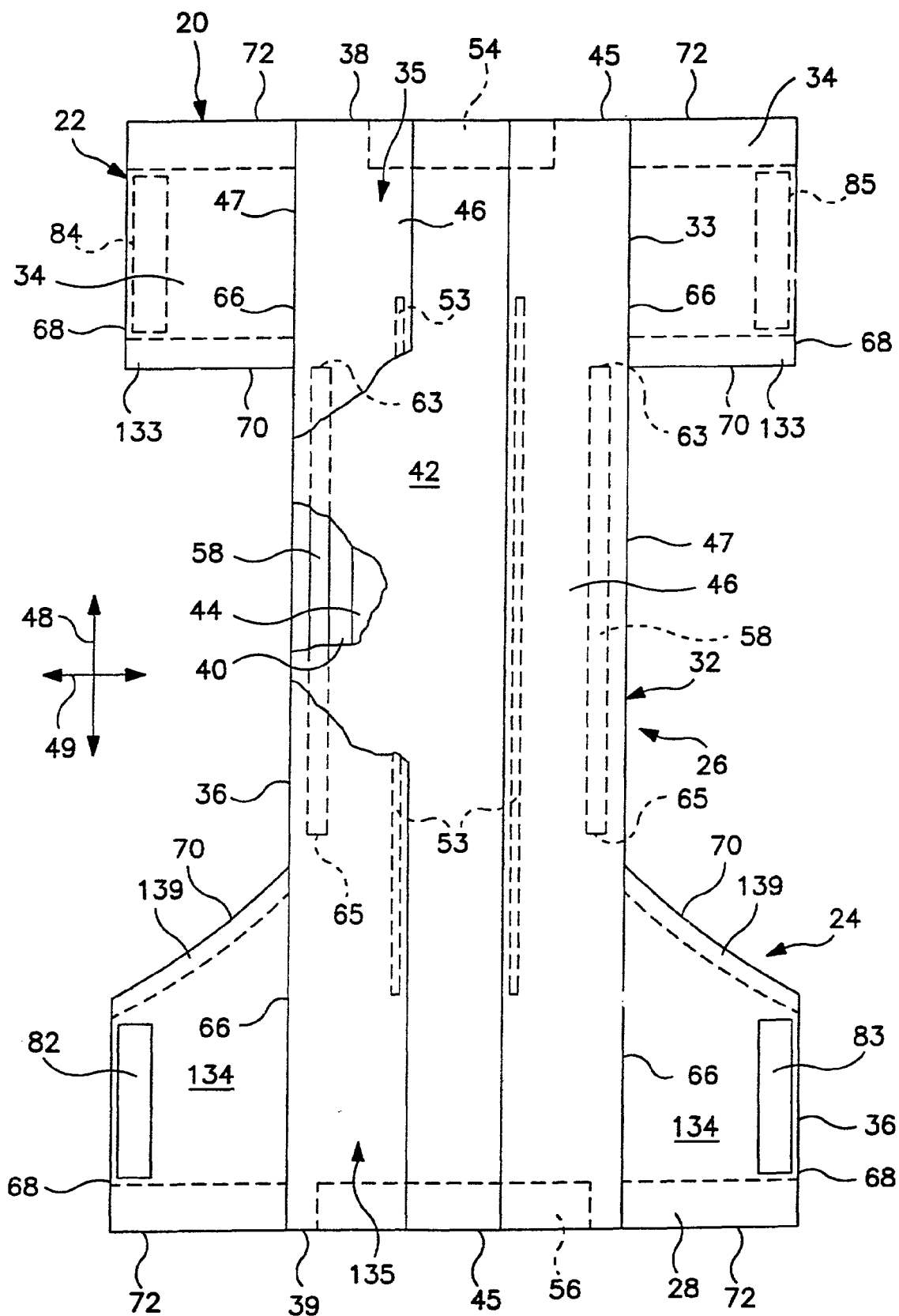
FIG. 4 is a plan view of the garment shown in FIG. 1, showing the side facing the wearer.

The illustrated absorbent chassis 32 comprises a rectangular absorbent composite structure 33, a pair of transversely opposed front side panels 34, and a pair of transversely opposed back side panels 134. The composite structure 33 and side panels 34 and 134 may be integrally formed or comprise two or more separate elements, as shown in FIG. 1. The illustrated composite structure 33 comprises an outer cover 40, a bodyside liner 42 (FIGS. 1 and 4) which is connected to the outer cover in a superposed relation, an absorbent assembly 44 (FIG. 4) which is located between the outer cover and the bodyside liner, and a part of containment flaps 46 (FIG. 4). The rectangular composite structure 33 has opposite linear end edges 45 that form portions of the front and back waist edges 38 and 39, and opposite linear side edges 47 that form portions of the side edges 36 of the absorbent chassis 32 (FIGS. 3 and 4). For reference, arrows 48 and 49 depicting the orientation of the longitudinal axis and the transverse axis, respectively, of the training pant 20 are illustrated in FIGS. 3 and 4.

With the training pant 20 in the fastened position as illustrated in FIG. 1, the front and back waist regions 22 and 24 are joined together to define a three-dimensional pant configuration having a waist opening 50 and a pair of leg openings 52. The front waist region 22 includes the portion of the training pant 20 which, when worn, is positioned on the front of the wearer while the back waist region 24 includes the portion of the training paint which, when worn, is positioned on the back of the wearer. The crotch region 26 of the training pant 20 comprises the portion of 110 the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 3 and 4) positioned between and interconnecting the side panels. The back waist region 24 of the absorbent chassis 32 includes the transversely opposed back side panels 134 and a back center panel 135 (FIGS. 3 and 4) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily includes the pair of containment flaps 46 which are configured to provide a barrier to the transverse flow of body exudates. A flap elastic member 53 (FIG. 4) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 4). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and to the leg elastic members 58 can be formed of any suitable elastic material, such as the targeted elastic material of the invention or separately manufactured and separately attached elastic materials. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and are available from E.I. Du Pont de Nemours and Company, Wilmington, Del., U.S.A., and other components of the garment, such as the side panels 55 comprise the targeted elastic material of the invention.

In the embodiment shown in FIG. 1, the front and back side panels 34 and 134 are fastened together by fastening system 88 to form collective side panels 55 (with each collective side panel 55 including a front side panel 34 and back side panel 134). In alternate embodiments, the collective side panels 55 may be single-piece side panels, or may include more than one piece permanently joined together. The transversely opposed front side panels 34 and transversely opposed back side panels 134 can be permanently bonded to the composite structure 33 of the absorbent chassis 32 in the respective front and back waist regions 22 and 24. More particularly, as shown best in FIGS. 3 and 4, the front side panels 34 can be permanently bonded to and extend transversely beyond the linear side edges 47 of the composite structure 33 in the front waist region 22 along attachment lines 66, and the back side panels 134 can be permanently bonded to and extend transversely beyond the linear side edges of the composite structure in the back waist region 24 along attachment lines 66. The side panels 34 and 134 may be attached using attachment means known to those skilled in the art such as adhesive, thermal or ultrasonic bonding. The side panels 34 and 134 can also be formed as a portion of a component of the composite structure 33, such as the outer cover or the bodyside liner. The fastening system 88 may include a plurality of fastener tabs 82, 83, 84 and 85, which can be known hook-and-loop fastener members, or other types of mechanical fasteners or adhesive fasteners. Alternatively, the front and back side panels 34, 134 can be permanently bonded together.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to the distal edge 68, as is best shown in FIGS. 3 and 4.

In accordance with the invention, the front side panels 34 each include a main body portion 130, an apparent elastic band 131 in the vicinity of the waist opening 50, and an apparent elastic band 133 in the vicinity of the leg opening 52. The rear side panels 134 each include a main body portion 136, an apparent elastic band 137 in the vicinity of the waist opening 50, and an apparent elastic band 139 in the vicinity of the leg opening 52. The invention encompasses a garment having at least one apparent elastic band. In alternate embodiments, for instance, the apparent elastic band or bands may be present only in the vicinity of the waist opening 50, or only in the vicinity of the leg openings 52.

As shown in FIGS. 1, 3 and 4, the apparent elastic bands 131 and 137 in the vicinity of waist opening 50 may be aligned with waist elastics 54 and 56 on the front and back of chassis 32, to create the visual impression of a continuous, or substantially continuous elastic band encircling the waist opening 50. Similarly, apparent elastic bands 133 and 139 in the vicinity of leg openings 52 can be aligned with leg elastics 58 to create the visual perception of continuous, or substantially continuous elastic bands encircling the leg openings. In the embodiment shown, actual elastic bands may substantially align with apparent elastic bands to create this perception. In other embodiments, apparent elastic bands may alone create the perception that an elastic band, whether continuous or not, is present.

The apparent elastic bands 131, 133, 137 and 139 exhibit greater elastic tension than the main portions 130 and 136 of side panels 34 and 134, without requiring the use of separately manufactured and attached elastic materials. The side panels 34 and 134 are manufactured from a targeted elastic material. Various embodiments of targeted elastic materials include the targeted elastic laminate materials shown in FIGS. 5-8. Referring to FIG. 5, TEL 100 (shown in sectional view, with the layers expanded apart from each other for clarity) includes a nonwoven layer 110 of elastomeric polymer filaments made from a single elastic polymer or polymer blend, laminated to at least one, desirably two outer facing layers 120. TEL 100 includes a low tension central zone 102 (which may correspond to body region 136 in side panel 134 of FIG. 1), a first high tension end zone 104 (which may correspond to apparent elastic region 139 in FIG. 1) and a second high tension end zone 106 (which may correspond to apparent elastic region 137 in FIG. 1). In the embodiment of FIG. 5, the polymer filaments 108 in the low tension zone 102 are spaced further apart and, thus define a lower basis weight per unit area of nonwoven web 110. The polymer filaments 108 in the high tension zones 104 and 106 are spaced more closely together and, thus, define a higher basis weight per unit area of nonwoven layer 110. Except for the spacing between filaments (and the resulting variation in nonwoven web basis weight), the polymer filaments 108 may be identical in size and composition. The elastomeric nonwoven layer 110 may be stretched in the machine direction (i.e., a direction parallel to the longitudinal orientation of filaments 108) prior to bonding nonwoven layer 110 to the facing layers 120 using processes as described below. After the layers are bonded together, the laminate may be relaxed (allowing retraction) and extended again as needed.

The TEL 100, when viewed by itself or in garment 20, would exhibit no visible perception of the high tension zones 104 and 106 as distinguished from the low tension zone 102. Instead, TEL 100 would appear as a homogeneous material, particularly when viewed from an outer surface of one of the facing layers 120. Yet the high tension zones 104 and 106 may function and perform as an elastic waist band and an elastic leg band, (i.e., may exhibit elasticity and elastic tension as would be provided by separately manufactured elastic bands). In order to create apparent elastic bands 131, 133, 137 and 139 as shown in FIG. 1, the high tension regions 104 and 106 of laminate 100 (FIG. 5) may be covered on both sides with a long, narrow band 125 of relatively inexpensive, suitably stretchable or extendible material. The material 125 need not exhibit elastic properties, but should be capable of stretching or extending, as needed, to keep up with any stretching of high tension regions 104 and 106 during use of TEL 100. For instance, stretchable material 125 may be an inelastic yet stretchable or extendible nonwoven web or other fabric. In one embodiment, stretchable material 125 may be a neck-stretched spunbond web as described in U.S. Pat. No. 4,965,122, issued to Morman, the disclosure of which is incorporated by reference. The neck-stretched nonwoven web may be formed from polypropylene, polyethylene, another polyolefin, or another relatively inexpensive thermoplastic polymer.

In the garment of FIG. 1, the band of material 125, placed over the TEL 100 of FIG. 6, can be used to form side panels 130 and 136 having apparent elastic bands 131, 133, 137 and 139. The apparent elastic bands look like elastic bands, and perform like elastic bands. However, they are not elastic bands as defined above or as known in the art, since they are not separately manufactured from an elastic material and then attached to the garment. Furthermore, the stretchable material 125 may be placed around the entire waist opening 50 (i.e., over the front and back waist edges 38 and 39 as well as over the upper edges of side panels 130 and 136) to create the visual perception of a single, continuous elastic band surrounding the waist opening. Additional pieces of stretchable material 125 may be placed around the entire leg openings 52 (i.e., over the edges of outer cover 40 as well as over the lower edges of side panels 130 and 136) to create the visual perception of a single continuous elastic band surrounding each leg opening.

Figure 2:
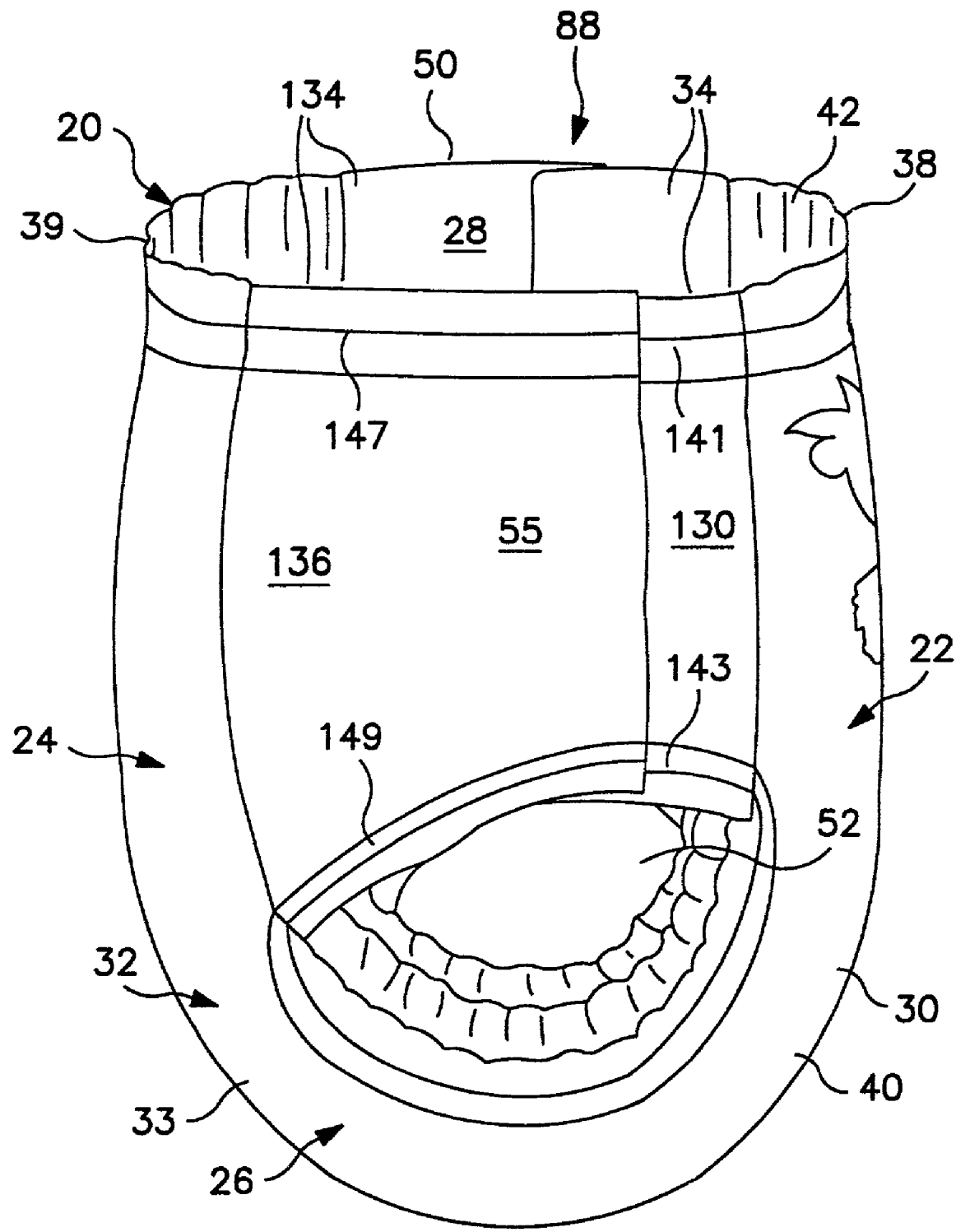
FIG. 2 illustrates another embodiment of a pant-like absorbent garment of the invention.

FIG. 2 illustrates an alternative embodiment of the garment of FIG. 1. Most of the elements in FIG. 2 are the same as in FIG. 1. As with FIG. 1, a TEL material (such as shown in FIG. 5) can be used to form the side panels 34 and 134. The only difference is that the apparent elastic bands 141, 143, 147 and 149 in FIG. 2 are not formed by adding a layer of stretchable material 125 over the high tension zones 104 and 106 of TEL 100. The stretchable layer 125 is not present. Instead, the apparent elastic bands are formed by providing bands of pigment in or over high tension zones 104 and 106. The pigment used to form apparent elastic bands 141, 143, 147 and 149 should be of a different color than the pigment (if any) visible in the low tension region 102 of the laminate. The pigment used to form the apparent elastic bands may be blue, black, yellow, green, brown, or any color which a consumer may perceive as indicating the presence of elastic bands. The pigment may be mixed with and extruded with the high tension polymer filaments defining the high tension zones 104 and 106, and may be visible through the facing layers 120. Alternatively, the pigment may be painted or printed onto a facing layer 120, or applied as an adhesive tape or other technique. Again, the pigment may be applied around the entire waist opening 50, and/or around each leg opening 52, to create the visual perception of continuous elastic bands surrounding the openings.

In still another embodiment, the principles of FIGS. 1 and 2 may be combined in a single product. Specifically, the stretchable material 125 shown in FIG. 5 can be colored with a pigment to provide apparent elastic bands with not only the visible perception, but also the touch and feel of actual elastic bands. The bands 125 can be affixed to TEL 100 by sewing, ultrasonic bonding, thermal bonding, adhesive bonding, or another technique.

In an absorbent product with targeted elastic side panels, it is desirable to match the targeted elastic portion of the elastic side panel to a printed or actual waistband on the outer cover (i.e., the front and back waist edges, and/or the outer cover edges at the leg openings). This gives the appearance of a continuous waistband resulting in the product having a more underwear-like appearance. When manufacturing a product in this way, matching (registering) the targeted elastic portion of the side panel to a printed or actual waistband on the outer cover cannot be done precisely. This misalignment of the targeted elastic and printed waistband detracts from the perception of quality a consumer would have of the product.

Overlaying an aesthetic, non-functional, stretchable material 125 on both the side panels and outer cover eliminates the problem of aligning the targeted elastic portion of the side panel to a printed or actual waistband on the outer cover. The continuous band of stretchable material 125 covers up any misalignment of the adjacent regions, and thereby enhances the quality look of the product.

Figure 7:
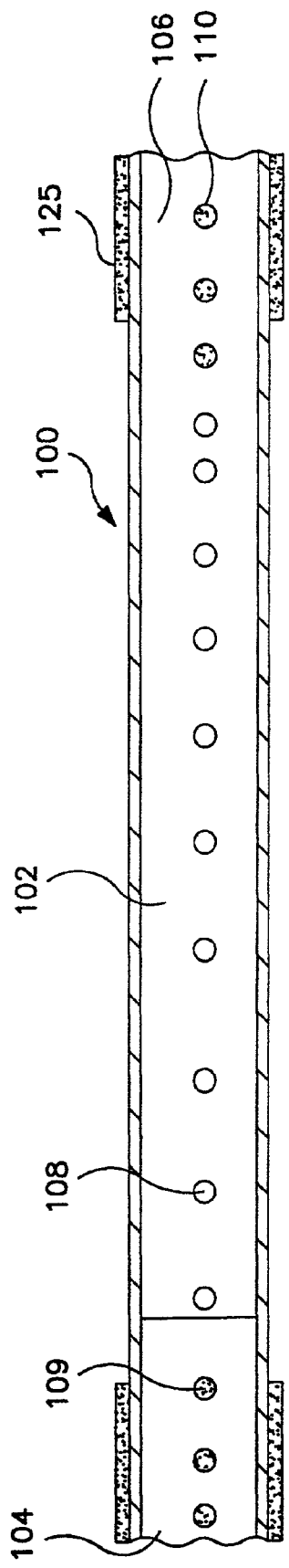
Figure 8:
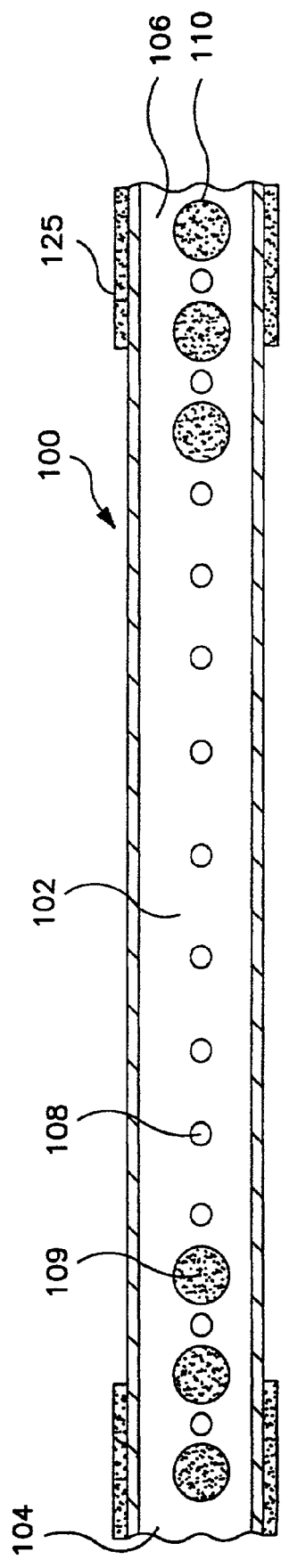

FIGS. 6-8 illustrate alternative embodiments of TEL materials which can be used with the bands 125 of stretchable material to make the garment of FIG. 1, or without the bands 125 but, instead, with added pigment to make the garment of FIG. 2. In FIG. 6, the high and low tension zones of TEL 100 are accomplished using polymer films of different sizes to achieve the higher nonwoven basis weights in high tension zones 104 and 106 and the lower nonwoven basis weight in the low tension zone 102. Specifically, the polymer filaments 109 in high tension regions 104 and 106 have larger diameters than the polymer filaments 108 in the low tension zone 102. In either FIG. 5 or FIG. 6, the high and low tension zones can be achieved via the same principle, by using nonwoven webs of different basis weights.

In the TEL of FIG. 7, the low and high tension zones 102, 104 and 106 are accomplished by forming the nonwoven layer 110 with two different elastic polymers or polymer blends, each one having a different elastic tension when stretched. The filaments 108 in low tension zone 102 are formed from a first elastic polymer or polymer blend. The filaments 109 in high tension zones 104 and 106 are formed from a second elastic polymer or polymer blend. Because different elastic polymers or polymer blends are used, the nonwoven layer 10 may have the same or different basis weights, the same or different filament sizes, and the same or different filament spacings in the low and high tension zones 102, 104 and 106.

The laminates of FIGS. 5-6 may each be produced by extruding the filaments 108 and 109 of nonwoven layer 110 from a single die, having die plate openings sized and spaced to correspond to the desired filament sizes and spacing, or from two or more different dies. The laminate of FIG. 7 may be produced by extruding filaments from either the same die fed by two or more polymer extruders, or from different dies for each polymer. Some of the processes described below illustrate how this is accomplished. In the laminate of FIG. 8, the nonwoven layer 110 may be formed by extruding two narrower bands of higher tension filaments 109 over a single wider band of lower tension filaments 108, using different dies and extruders. The result, shown in FIG. 8, is that low tension zone 102 contains only low tension filaments formed of a first elastic polymer or polymer blend. High tension zones 104 and 106 contain both high tension filaments 109 formed of a second elastic polymer or polymer blend, and low tension filaments 108.

In TEL 100, low tension zone 102 may have a first elastic tension, measured at 50% elongation of the filaments, and high tension zones 104 and 106 may have second and third elastic tensions higher than the first tension, measured at the same elongation. At 50% elongation of the TEL 100 (in the machine direction, parallel to filament orientation), high tension zones 104 and 106 may have an elastic tension at least 10% greater, suitably at least 50% greater, desirably 100-800% greater, or about 125-500% greater, or as another alternative about 150-300% greater than the low tension zone 102. Elastic tension may be measured, for instance, using an MTS Sintec Model 1/s, available from MTS in Research Triangle Park, N.C., with a crosshead speed set to 500 mm/min. Samples having a 3-inch width and 6-inch length can be used, with 3 inches of the length clamped inside the jaws (leaving 3 inches of length for testing). The tension of each high and low tension region can be measured after the portion of the TEL laminate being tested is held in the extended condition (in the machine direction of the TEL) for 60 seconds.

In the TEL embodiments where the low and high tension zones are formed from nonwoven web sections having different basis weights (FIGS. 5-6), the nonwoven basis weights in the high tension zones 104 and 106 may be at least 10% greater, suitably at least 50% greater, desirably 100-800% greater, alternatively 125-500% greater, or as another alternative 200-400% greater than the nonwoven basis weight in the low tension zone 102. For instance, the nonwoven in the low tension zone may have a basis weight of about 2-14 grams per square meter (gsm), desirably about 4-12 gsm. In the high tension zones 104 and 106, the nonwoven basis weight may be about 10-32 gsm, desirably about 12-30 gsm. If the higher and lower basis weights are achieved using spinning holes of different frequency in the die, resulting in a higher areal density of filaments in the high tension regions and lower areal density of filaments in the low tension region, then the higher areal density may be at least 10% greater, suitably at least 50% greater, desirably 100-800% greater, alternatively 125-500% greater, or as another alternative 200-400% greater than the lower areal density. The filament density in each zone may range from about 4-40 filaments per square inch (fsi), suitably about 12-30 fsi, measured perpendicular to the length of the filaments.

If the higher and lower basis weights are achieved using filaments of higher and lower diameters, as in FIG. 6, the higher diameter filaments 109 may have diameters at least 5% higher, suitably at least 20% higher, desirably 40-300% higher, alternatively 50-125% higher, or as another alternative 75-100% higher than the lower diameter filaments 108. The filament diameters in each zone may range from about 0.010-0.040 inch, suitably about 0.020-0.032 inch.

If the higher and lower tension zones are formed using nonwoven filaments 108 and 109 of different elastic polymer composition, as shown in FIG. 7, then the different elastic polymers or polymer blends should be selected to give the desired higher elastic tension in the high tension zones 104 and 106 and the desired lower elastic tension in the low tension zone 102. The nonwoven basis weights in the different zones may be the same or different, and may be adjusted, along with the polymer compositions, to achieve the desired elastic tensions. When a polymer blend is used, the blend itself should exhibit the desired elastic tension, regardless of the properties of the individual components.

Materials suitable for use in preparing elastomeric filaments 108 and 109 in the low and high tension zones 102, 104 and 106, include diblock, triblock, tetrablock or other multiblock elastomeric copolymers such as olefinic copolymers, including styrene-isoprene-styrene, styrene-butadiene-styrene, styreneethylene/butylene-styrene, or styrene-ethylene/propylene-styrene, which may be obtained from the Shell Chemical Company, under the trade designation KRATON® elastomeric resin; polyurethanes, including those available from B.F. Goodrich Co., under the trade name ESTANE®; polyamides, including polyether block amides available from Ato Chemical Company, under the trade name PEBAX® polyether block amide; polyesters, such as those available from E.I. Du Pont de Nemours Co., under the trade name HYTREL® polyester; and single-site or metallocene-catalyzed polyolefins having density less than about 0.89 grams/cc, available from Dow Chemical Co. under the trade name AFFINITY®.

A number of block copolymers can be used to prepare thermoplastic elastomeric filaments 108, 109 useful in this invention. Such block copolymers generally comprise an elastomeric midblock portion B and a thermoplastic endblock portion A. The block copolymers may also be thermoplastic in the sense that they can be melted, formed, and resolidified several times with little or no change in physical properties (assuming a minimum of oxidative degradation).

Endblock portion A may comprise a poly(vinylarene), such as polystyrene. Midblock portion B may comprise a substantially amorphous polyolefin such as polyisoprene, ethylene/propylene polymers, ethylene/butylene polymers, polybutadiene, and the like, or mixtures thereof.

Suitable block copolymers useful in this invention include at least two substantially polystyrene endblock portions and at least one substantially ethylene/butylene mid-block portion. A commercially available example of such a linear block copolymer is available from the Shell Chemical Company under the trade designation KRATON® G1657 elastomeric resin. Another suitable elastomer is KRATON® G2740.

Other suitable elastomeric polymers may also be used to make thermoplastic elastomeric filaments 108, 109. These include, without limitation, elastomeric (single-site or metallocene catalyzed) polypropylene, polyethylene and other alpha-olefin homopolymers and copolymers, having density less than about 0.89 grams/cc; ethylene vinyl acetate copolymers; and substantially amorphous copolymers and terpolymers of ethylene-propylene, butene-propylene, and ethylenepropylene-butene.

Single-site catalyzed elastomeric polymers (for example, constrained geometry or metallocene-catalyzed elastomeric polymers) are available from Exxon Chemical Company of Baytown, Tex., and from Dow Chemical Company of Midland, Mich. The single-site process for making polyolefins uses a single-site catalyst which is activated (i.e., ionized) by a co-catalyst.

Commercial production of single-site catalyzed polymers is somewhat limited but growing. Such polymers are available from Exxon Chemical Company of Baytown, Tex. under the trade name EXXPOL® for polypropylene based polymers and EXACT® for polyethylene based polymers. Dow Chemical Company of Midland, Mich. has polymers commercially available under the name ENGAGE®. These materials are believed to be produced using non-stereo selective single-site catalysts. Exxon generally refers to their single-site catalyst technology as metallocene catalysts, while Dow refers to theirs as "constrained geometry" catalysts under the name INSITE® to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade.

Elastic filaments 108 and 109 may also contain blends of elastic and inelastic polymers, or of two or more elastic polymers, provided that the blend exhibits elastic properties. The filaments may be substantially continuous or staple in length, but are desirably substantially continuous. Substantially continuous filaments have better elastic recovery than staple length filaments. Elastic filaments 108 and 109 may be circular but may also have other cross-sectional geometries such as elliptical, rectangular, triangular or multi-lobal. In one embodiment, one or more of the filaments may be in the form of elongated, rectangular film strips produced from a film extrusion die having a plurality of slotted openings.

The facing layer or layers 120 may each include a nonwoven web, for example a spunbonded web or a meltblown web, a woven web, or a film. Facing materials may be formed using conventional processes, including the spunbond and meltblowing processes described in the "DEFINITIONS." For example, facing materials 120 may include a spunbonded web having a basis weight of about 0.1-4.0 osy, suitably 0.2-2.0 osy, desirably about 0.4-0.6 osy. The facing materials 120 may include the same or similar materials or different materials.

The facing materials 120 can be bonded to a nonwoven layer 110 (including the low and high tension zones thereof) using an adhesive, for example an elastomeric adhesive such as Findley H2525A, H2525 or H2096. Other bonding means well known to those having ordinary skill in the art may also be used to bond the facing materials 120 to filaments 108 and 109 of nonwoven web 110, including thermal bonding, ultrasonic bonding, mechanical stitching and the like. Many of the same techniques can be used to bond the stretchable band materials 125 to the surface of facing layers 120.

Figure 9:
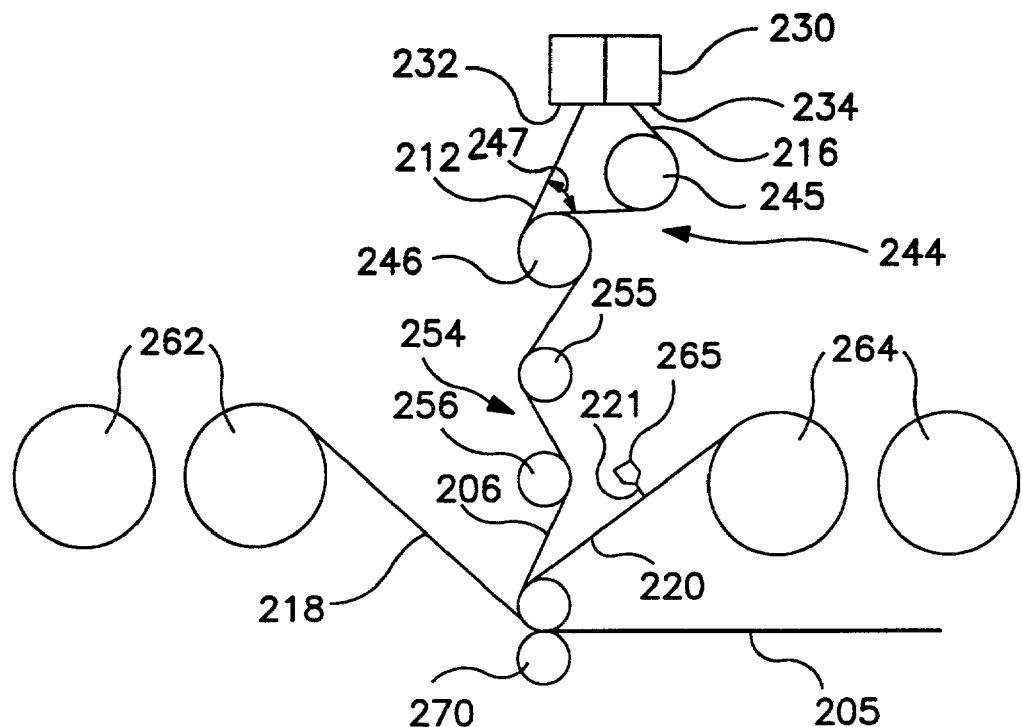
FIGS. 9-12 illustrate representative processes for making TEL materials useful for making garments having apparent elastic bands.
Figure 10:
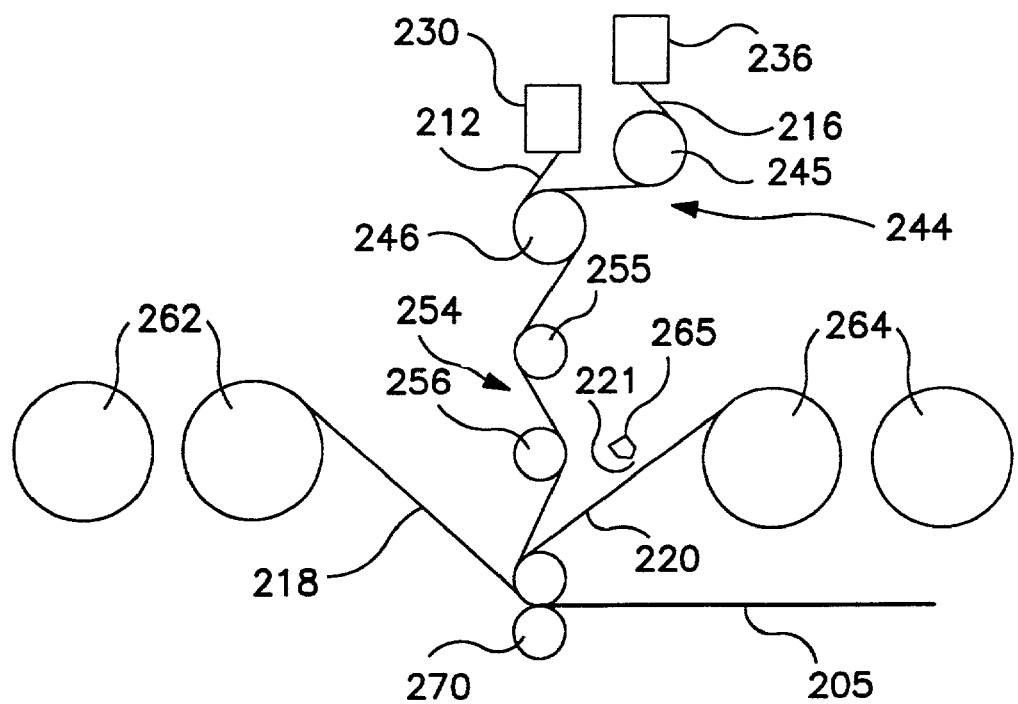

FIGS. 9-12 and 16 illustrate representative processes for making TEL materials. FIGS. 9 and 10 each illustrate a vertical filament stretch-bond laminate (VF SBL) method. Referring to FIG. 9, an extruder (not shown) supplies molten elastomeric material to a first die 230. First die 230 includes different regions of spinning holes tailored to provide the nonwoven fabric 206 with higher and lower zones of elastic tension, having higher and lower basis weights or different polymer compositions as explained with respect to FIGS. 5-8.

Referring to FIG. 9, molten elastomeric material is extruded from first spin plate region 232 through spinning holes as a plurality of elastomeric first filaments 212. Similarly, a plurality of elastomeric second filaments 216 are extruded from second spin plate region 234 through spinning holes of different average diameter, different frequency, and/or different polymer composition. The resulting nonwoven web 206 has a higher elastic tension in the zone defined by second filaments 216, than in the zone defined by first filaments 212. After extruding, first and second filaments 212 and 216 are quenched and solidified.

In one embodiment, first and second filaments 212 and 216 are quenched and solidified by passing them over a first series of chill rolls 244. For instance, first filaments 212 may be contacted with chill roll 246. Second filaments 216, having a higher aggregate basis weight, may be passed over two chill rolls 245 and 246. Any number of chill rolls can be used. Suitably, chill rolls 245 and 246 have a temperature of about 40° F. to about 80° F.

The die of each extruder may be positioned with respect to the first roller so that the continuous filaments meet this first roller at a predetermined angle 247. This strand extrusion geometry is particularly advantageous for depositing a melt extrudate onto a rotating roll or drum. An angled, or canted, orientation provides an opportunity for the filaments to emerge from the die at a right angle to the roll tangent point resulting in improved spinning, more efficient energy transfer, and generally longer die life. This improved configuration allows the filaments to emerge at an angle from the die and follow a relatively straight path to contact the tangent point on the roll surface. The angle 247 between the die exit of the extruder and the vertical axis (or the horizontal axis of the first roller, depending on which angle is measured) may be as little as a few degrees or as much as 90°. For example, a 90° extrudate exit to roller angle could be achieved by positioning the extruder directly above the downstream edge of the first roller and having a side exit die tip on the extruder. Moreover, angles such as about 20°, about 35°, or about 45° away from vertical may be utilized. It has been found that, when utilizing a 12-filament/inch spinplate hole density, an approximately 45° angle (shown in FIG. 9) allows the system to operate effectively. The optimum angle, however, will vary as a function of extrudate exit velocity, roller speed, vertical distance from the die to the roller, and horizontal distance from the die centerline to the top dead center of the roller. Optimal performance can be achieved by employing various geometries to result in improved spinning efficiency and reduced filament breakage. In many cases, this results in potentially increased roll wrap resulting in more efficient energy transfer and longer die life due to reduced drag and shear of the extrudate as it leaves the capillaries of the extruder die and proceeds to the chilled roll.

After first and second filaments 212 and 216 are quenched and solidified, they are stretched or elongated. In one desired embodiment, first and second filaments 212 and 216 are stretched using a first series of stretch rolls 254. First series of stretch rolls 254 may include one or more individual stretch rolls 255, desirably at least two stretch rolls 255 and 256, as shown in FIG. 9. Stretch rolls 255 and 256 rotate at a speed greater than a speed at which chill rolls 245 and 246 rotate, thereby stretching the nonwoven fabric 206, including the zones of first and second filaments 212 and 216.

In one embodiment, each successive roll rotates at a speed greater than the speed of the previous roll. For example, referring to FIG. 9, chill roll 245 rotates at a speed "x"; chill roll 246 rotates at a speed greater than "x", for example about "1.1x"; stretch roll 255 rotates at a still greater speed, for example about "1.15x"; second stretch roll 256 rotates at a still greater speed, for example about "1.25x" to about "2x"; and a third stretch roll (not shown) rotates at a still greater speed, for example about "2x" to about "7x." As a result, first and second filaments 212 and 216 can be stretched by about 100% to about 800% of an initial length, or by about 200% to about 700% of an initial length.

After first and second filaments 212 and 216 are stretched, elastic nonwoven web 206 is laminated to a first facing material 218 and (alternatively) a second facing material 220. First facing material 218 is unwound from one of the rollers 262 and laminated to a first side of nonwoven web 206. Second facing material 220 is unwound from one of the rollers 264 and laminated to a second side of nonwoven web 206. As shown in FIG. 9, before second facing material 220 is laminated to a second side of elastic nonwoven web 206, at least a portion of second facing material 220 can be coated or sprayed with an elastomeric adhesive 221, such as Findley H2525A, H2525 or H2096, via an adhesive sprayer 265. The laminate material is then passed through nip rolls 270 (desirably smooth calender rolls) and is relaxed and/or retracted to produce a TEL 205. Other means for bonding the laminate material known to those having ordinary skill in the art may be used in place of nip roll 270.

FIG. 10 illustrates a VF SBL process similar to that of FIG. 9. In FIG. 10, instead of using a single spinnerette 230 having adjacent die regions for the high and low tension filament zones, two spinnerettes 230 and 236 are employed. First spinnerette 230 extrudes the first filaments 212. Second spinnerette 236 extrudes the second filaments 216. Again, the first and second spinnerettes differ as to the aggregate basis weights and/or polymer compositions of the elastomeric filaments produced. The second spinnerette 236 may have die openings of a) higher frequency and/or b) higher diameter, than the die openings of the first spinnerette 230. Except for the use of two spinnerettes instead of one "hybrid" spinnerette, the processes of FIGS. 9 and 10 are similar. In either case, the first filaments 212 and second filaments 216 ultimately converge to form a single elastic nonwoven web 206 having zones of higher and lower elastic tensions. The filaments 212 and 216 may converge in a side-by-side fashion as shown in FIGS. 5-7, for instance, to produce zones of higher and lower tension. Alternatively, the bands of filaments 212 and 216 may have different widths such that a narrower layer or band of second filaments 216 is superimposed directly over a wider layer band of filaments 212, so that the higher tension zone occurs where the two layers coexist as exemplified in FIG. 8. In either process, the first filaments 212 and second filaments 216 may converge as shown, at the chill roll 246.

Figure 16:
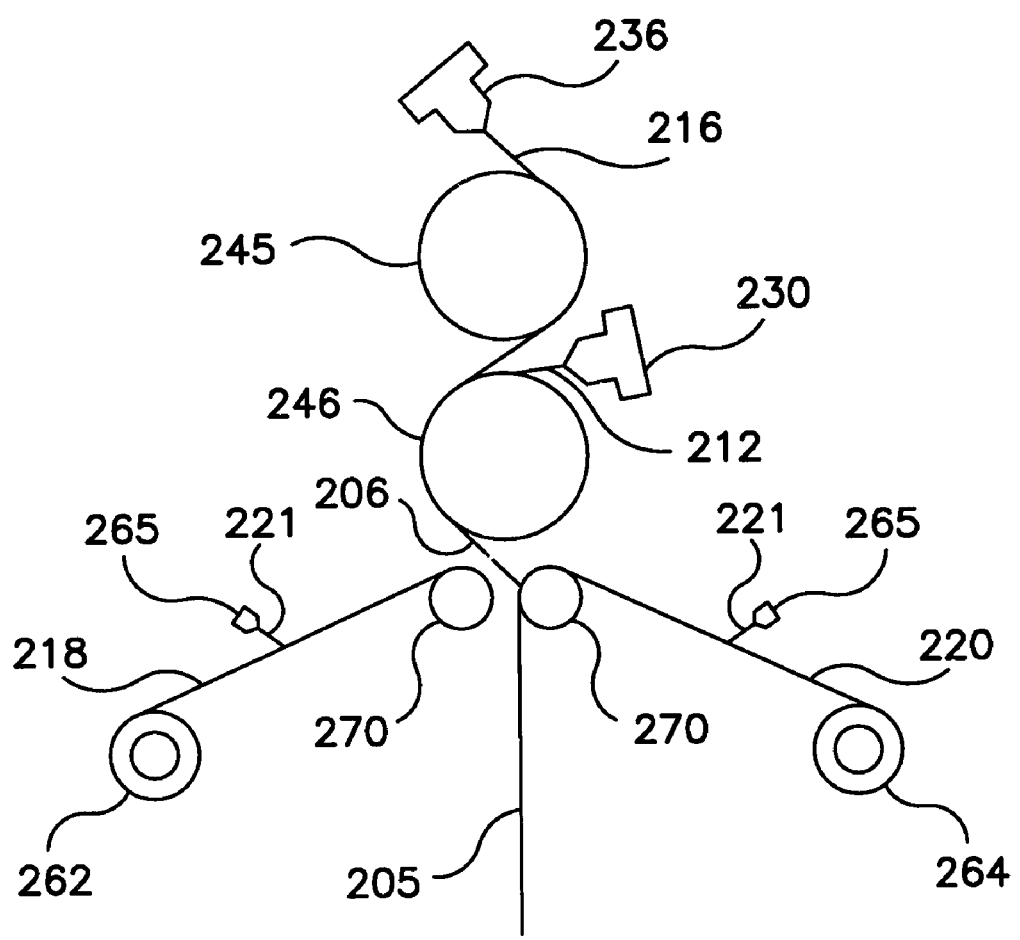
FIG. 16 is a schematic view of another process for making TEL materials useful for making garments having apparent elastic bands.

FIG. 16 illustrates a VF SBL process in which no stretch rolls 254 are used. Instead, first filaments 212 are extruded onto chill roll 246. Second filaments 216 are extruded onto chill roll 245, where the first filaments 212 and second filaments 216 converge to form a single elastic nonwoven layer 206 having zones of higher and lower elastic tensions. The first and second filaments 212, 216 are stretched between the chill rolls 245, 246 and the nip rolls 270. Except for the lack of stretch rolls 254, the processes of FIGS. 9 and 17 are similar. In either case, the elastic nonwoven layer 206 is laminated between a first facing layer 218 and a second facing layer 220 at the nip rolls 270. The resulting laminate is then relaxed and/or retracted to form TEL 205.

Figure 11:
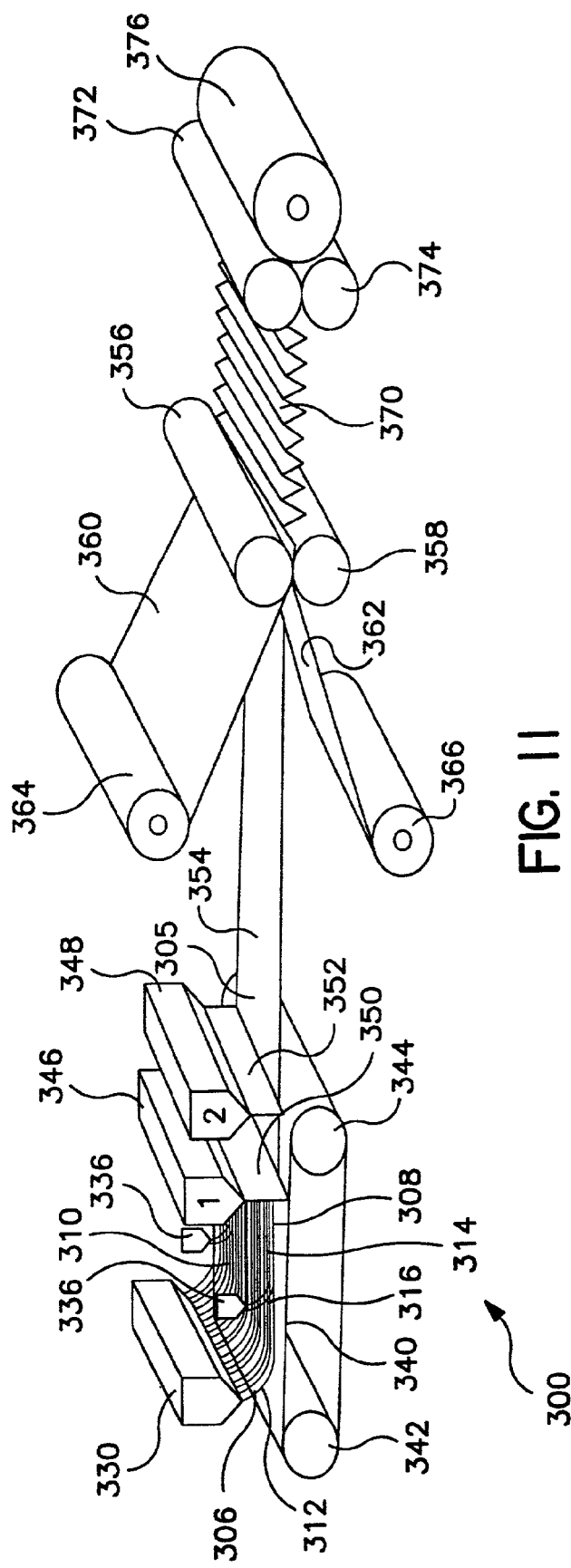

FIG. 11 illustrates a continuous horizontal filament stretch-bond laminate (CF SBL) process 300 for making TEL materials. A first extrusion apparatus 330 (which can be a spinnerette, as described above) is fed with an elastomeric polymer or polymer blend using one or more extruders (not shown). In various embodiments, the extrusion apparatus 330 can be configured to form a nonwoven layer 306 having zones of higher and lower elastic tension, as illustrated in FIGS. 5-8. In another embodiment, the extrusion apparatus 330 can be configured with die holes of uniform size and spacing, to yield a nonwoven layer 306 which has uniform elastic tension across its width. The nonwoven layer 306 contains filaments 312 which are substantially continuous in length. In this regard, the extrusion apparatus 330 may be a spinnerette. Suitably, apparatus 330 is a meltblowing spinnerette operating without the heated gas (e.g., air) stream which flows past the die tip in a conventional meltblowing process. Apparatus 330 extrudes filaments 312 directly onto a conveyor system, which can be a forming wire system 340 (i.e., a foraminous belt) moving clockwise about rollers 342. Filaments 312 may be cooled using vacuum suction applied through the forming wire system, and/or cooling fans (not shown). The vacuum may also assist in holding nonwoven layer 306 against the forming wire system.

In a desired embodiment, at least one, possibly two or more second extrusion apparatus 336 are positioned downstream of the first extrusion apparatus 330. The second extrusion apparatus create one or more higher tension zones in the nonwoven layer 306 by extruding filaments 316 of elastic material directly onto the nonwoven layer 306 in bands or zones which are narrower than the width of nonwoven layer 306. The second filaments 316 may be of the same elastic polymer construction as the first filaments 312. The extrusion of second filaments 316 over the first filaments 312 only in selected regions of layer 306, operates to create higher elastic tension zones 314 where the first and second filaments 312 and 316 coexist, and lower elastic tension zones 310 where the first filaments 312 exist alone. The first and second filaments 312 and 316 converge, and are combined in the forming conveyor 340 as it travels forward, to yield nonwoven layer 308 having at least one first zone 310 of lower elastic tension, and second, outer zones 314 of higher elastic tension.

As explained above, nonwoven layer 308 can be produced either a) directly from spinnerette 330, which is configured to yield zones of higher and lower elastic tension similar to FIGS. 3-7, or b) through the combined effects of spinnerette 330 as a uniform or nonuniform die, and secondary spinnerettes 336 which increase the elastic tension in localized regions of layer 308 by extruding secondary filaments 316 onto layer 306, similar to the web in FIG. 8. In either case, the nonwoven layer 308 (including filaments 312 and 316) may be incidentally stretched and, to an extent, maintained in alignment by moving the foraminous conveyor 340 in a clockwise machine direction, at a velocity which is slightly greater than the exit velocity of the filaments leaving the die.

To make the TEL 305, the elastic nonwoven layer 308 having higher and lower elastic tension zones is reinforced with one or more elastomeric meltblown layers made of the same or different elastic polymer material. Referring to FIG. 11, meltblowing extruders 346 and 348 are used to form meltblown layers 350 and 352 onto one side of web 308, resulting in TEL 305. The meltblown layer or layers may act as structural facing layers in the laminate, and/or may act as tie layers if it is desired to add still more layers to the laminate.

Several patents describe various spray apparatuses and methods that may be utilized in supplying the meltblown layers (adhesives) to the outer facing(s) or, when desired, to the elastic strands themselves. For example, the following United States patents assigned to Illinois Tool Works, Inc. ("ITW") are directed to various means of spraying or meltblowing fiberized hot melt adhesive onto a substrate: U.S. Pat. Nos. 5,882,573; 5,902,540; 5,904,298. These patents are incorporated herein in their entireties by reference thereto. The types of adhesive spray equipment disclosed in the aforementioned patents are generally efficient in applying the adhesive onto the nonwoven outer facings in the VFL process of this invention. In particular, ITW-brand Dynatec spray equipment, which is capable of applying about 3 gsm of adhesive at a run rate of about 1100 fpm, may be used in the melt-spray adhesive applications contemplated by the present inventive process.

Representative adhesive patterns are illustrated in FIGS. 13A through 15D. Applying an adhesive in a cross-machine pattern such as the ones shown in FIGS. 15C and 15D may result in certain adherence advantages. For example, because the elastic strands are placed in the machine direction, having the adhesive pattern orient to a large degree in the cross-machine direction provides multiple adhesives to elastic crossings per unit length.

In addition, in many particular embodiments of the present invention, the adhesive component is applied to the surface of the nonwoven layer in discrete adhesive lines. The adhesive may be applied in various patterns so that the adhesive lines intersect the elastic filament lines to form various types of bonding networks which could include either adhesive-to-elastic bonds or adhesive-to-elastic bonds, adhesive-to-facing layer, and adhesive-to-adhesive bonds. These bonding networks may include a relatively large total number of adhesive-to-elastic and adhesive-to-adhesive bonds that provide the laminated article with increased strength, while utilizing minimal amounts of adhesive. Such enhancements are achieved by the use of adhesive sprayed onto the surface of the nonwoven in a predetermined and specific pattern. In most cases, a final product with less adhesive exhibits a reduction in undesirable stiffness, and is generally more flexible and soft than products having more adhesive.

Figure 13D:
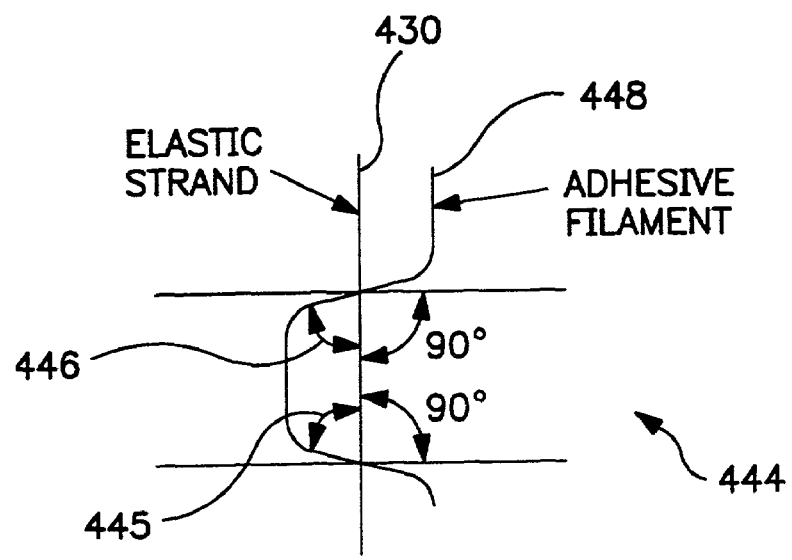
FIG. 13D shows an exemplary bond angle in one exemplary adhesive spray pattern.
Figure 14:
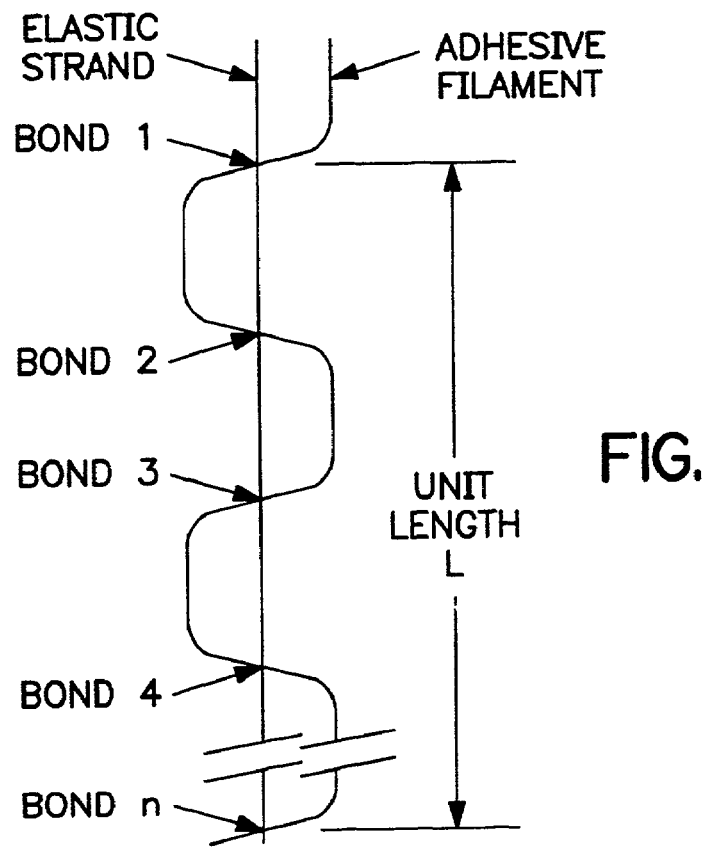
FIG. 14 illustrates the bonding pattern and method of calculating the number of bonds per unit length on elastic strands or filaments.

Applying the adhesive in a pattern so that the adhesive lines are perpendicular or nearly perpendicular to the elastic components has been found particularly advantageous. A true 90° bond angle may not be possible in practice, but an average or mean bond angle that is as great as 50° or 60° will generally produce a suitable bond between the elastic strands and the facing material. A conceptual illustration of these types of bond angles is shown in FIGS. 13D and 14. The adhesive-to-elastic bonds are formed where the lines of adhesive 448 and elastic strands 430 join or intersect.

The continuous adhesive filaments-to-elastic strand intersections are also controlled to a predetermined number of intersections per unit of elastic strand length. By having such adhesive lines in a perpendicular orientation and optimizing the number of bonds per unit of elastic strand length, the final elastic strand laminate can be produced with a minimal amount of adhesive and elastomeric strand material to provide desirable product characteristics at a lower cost.

If the adhesive-to-elastic bonds are too few in number or are too weak, then the elastic tension properties of the laminate may be compromised and the tension applied to the elastic strands may break the adhesive joints. In various known processes, the common remedy for this condition is to increase the number of bonding sites by either increasing the meltspray air pressure, or by slowing the lamination speed. As the meltspray air pressure is increased, the resulting adhesive fiber size is reduced, creating weaker bonds. Increasing the amount of adhesive used per unit area to create larger adhesive filaments can strengthen these weaker bonds, which usually increases the cost of the laminate. Lowering the lamination speed decreases machine productivity, negatively impacting product cost. The present invention, in part, utilizes an effective bonding pattern where the number of bond sites per length elastic strand are prescribed and where the adhesive-to-elastic strand joints are generally perpendicular in orientation in order to provide maximum adhesive strength. This allows the laminate to be made at minimal cost by optimizing the adhesive and elastomer content to match the product needs.

As used herein, a "scrim" refers generally to a fabric or nonwoven web of material which may be elastic or inelastic, and having a machine direction ("MD") oriented strand component along the path of product flow during manufacture and a cross-machine direction ("CD") strand component across the width of the fabric.

Figure 13A:
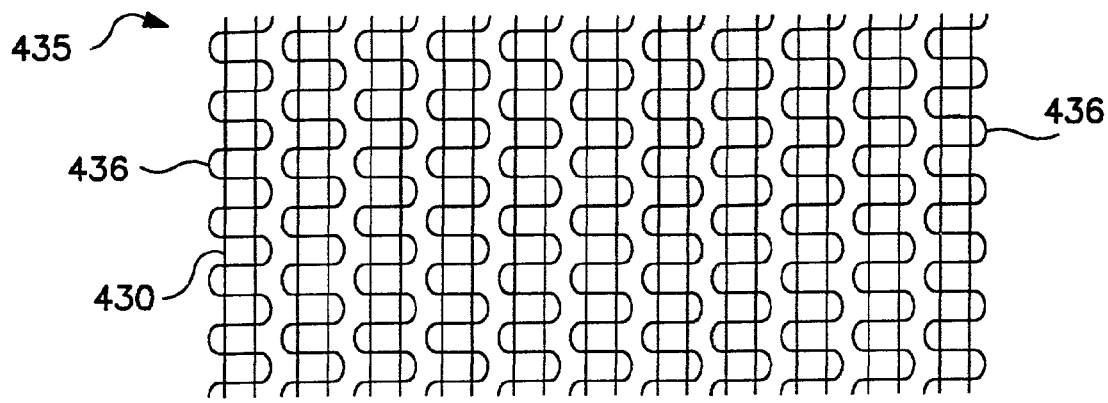
FIG. 13A shows one exemplary adhesive spray pattern in which the adhesive has been applied to the elastic filaments with attenuation in the cross direction.
Figure 13B:
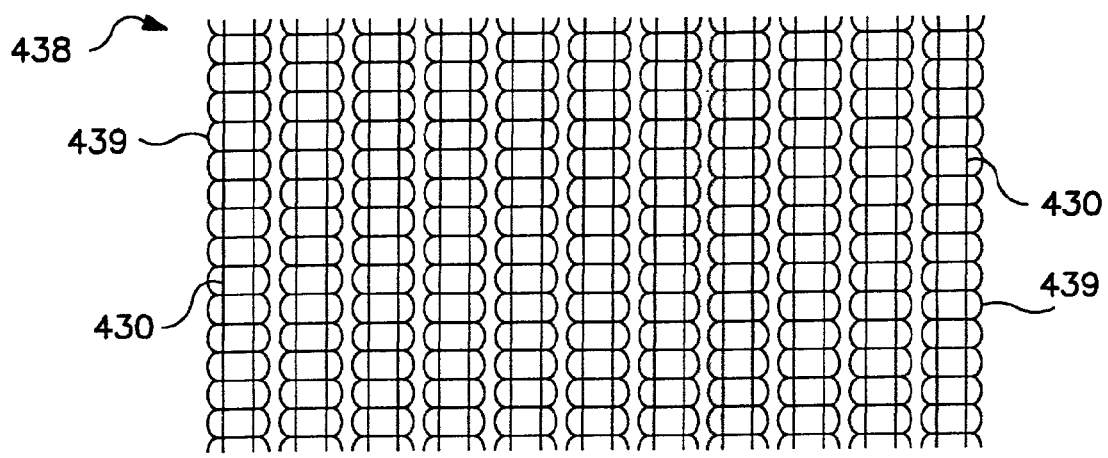
FIG. 13B shows a second exemplary adhesive spray pattern.
Figure 13C:
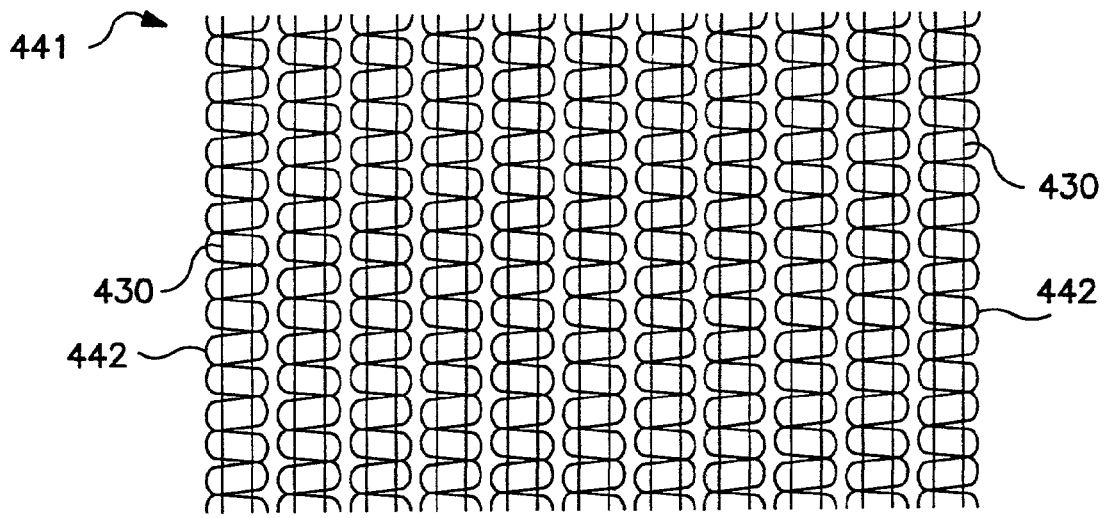
FIG. 13C illustrates a third exemplary adhesive spray pattern.

FIG. 13A shows one exemplary scrim pattern useful in the present invention in which the adhesive has been applied to the elastic filaments with attenuation of the adhesive lines in the cross-machine direction. Scrim pattern 435 includes adhesive line 436 and elastic filaments 430. FIG. 13B illustrates another exemplary scrim pattern 438 having adhesive lines 439 applied to elastic strands 430. In this embodiment, it can be seen that the bond angle is very high, approaching 90° at the intersection between the adhesive and the elastic filaments. FIG. 13C illustrates still another scrim pattern 441 having adhesive lines 442 and continuous elastic strands 430.

As previously discussed, FIG. 13D illustrates the relatively high bond angle that may be employed in products produced according to the present invention. In particular, lay down angle 444 is shown as the angle formed by the adhesive line 448 and the elastic strand 430. Adhesive/elastic angle 446 and adhesive/elastic angle 445 are shown as being less than 90°.

Figure 15A:
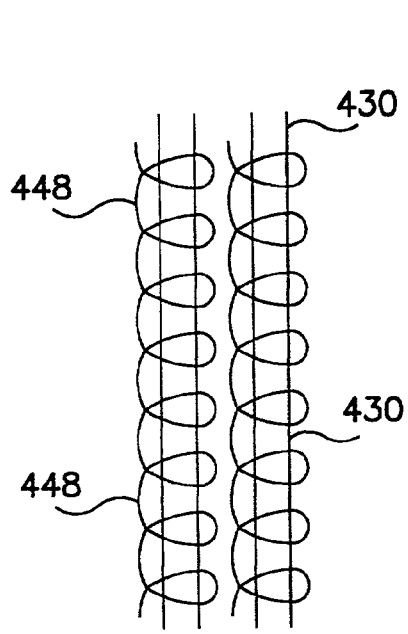
FIG. 15A shows a fourth exemplary adhesive spray pattern in a swirled-type of configuration.
Figure 15B:
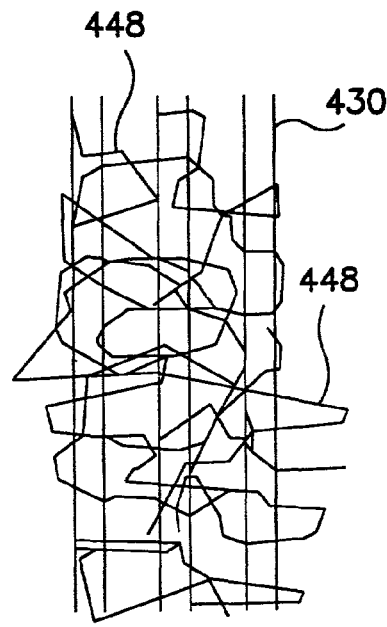
FIG. 15B shows a fifth exemplary adhesive spray pattern that is more randomized and which provides a large percentage of adhesive lines in a perpendicular orientation to the elastic filaments.
Figure 15C:
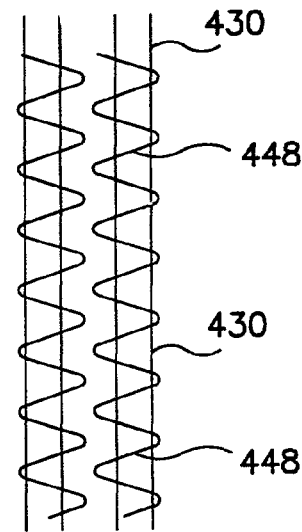
FIG. 15C illustrates a sixth exemplary adhesive spray pattern having attenuation of adhesive lines in the cross-machine direction.
Figure 15D:
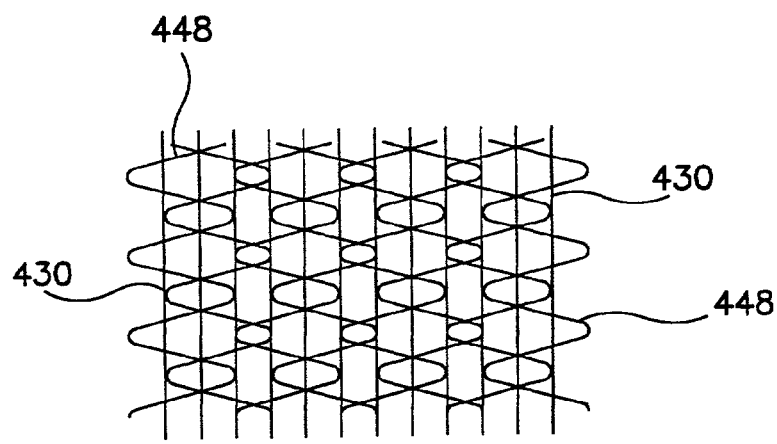
FIG. 15D shows a seventh exemplary adhesive spray pattern that resembles a "chain-link fence"

FIG. 14 utilizes an exemplary bonding pattern to conceptually illustrate the measurement for determining the number of bonds per unit length on elastic strands or filaments. FIG. 15A shows another exemplary bonding pattern having the adhesive-to-adhesive bonding wherein a swirled type of configuration is employed. FIG. 15B illustrates a more randomized pattern wherein a large percentage of adhesive lines are in a perpendicular, or almost perpendicular, orientation to the elastic filaments. FIG. 15C is another exemplary embodiment of a bonding pattern having no adhesive-to-adhesive bonds, but numerous adhesive-to-elastic strand bonds. FIG. 15D illustrates another exemplary bonding pattern that has both adhesive-to-adhesive and adhesive-to-elastic strand bonds. The configuration shown in FIG. 15D is similar to the design of a chain-link fence.

Then, if it is desired to convert the TEL 305 into a stretch-bonded laminate, the TEL 305 may be stretched in a stretching stage 354 by pulling it between two nip rolls 356 and 358 which turn at a higher surface speed than the conveyor 340. At the same time, the facing layers 360 and 362 can be unwound from supply rollers 364 and 366, and laminated to the TEL 305 using the stretch roll assembly. To accomplish this dual purpose, the nip rolls 356 and 358 may be calender rolls (suitably having smooth or patterned surfaces) which use pressure to bond the materials 360, 305 and 362 together as well as stretch the TEL 305. Alternatively, both heat and pressure may be applied to bond the materials 360, 305 and 362 together. The resulting stretch-bonded laminate 370 may then be relaxed and/or retracted using nip rollers 372 and 374 that rotate at lower surface speed than calender rolls 358, and may be wound onto storage roll 376. The facing layers 360 and 362 may be any of the facing materials described above, and are desirably polyolefin-based spunbond webs.

Figure 12:
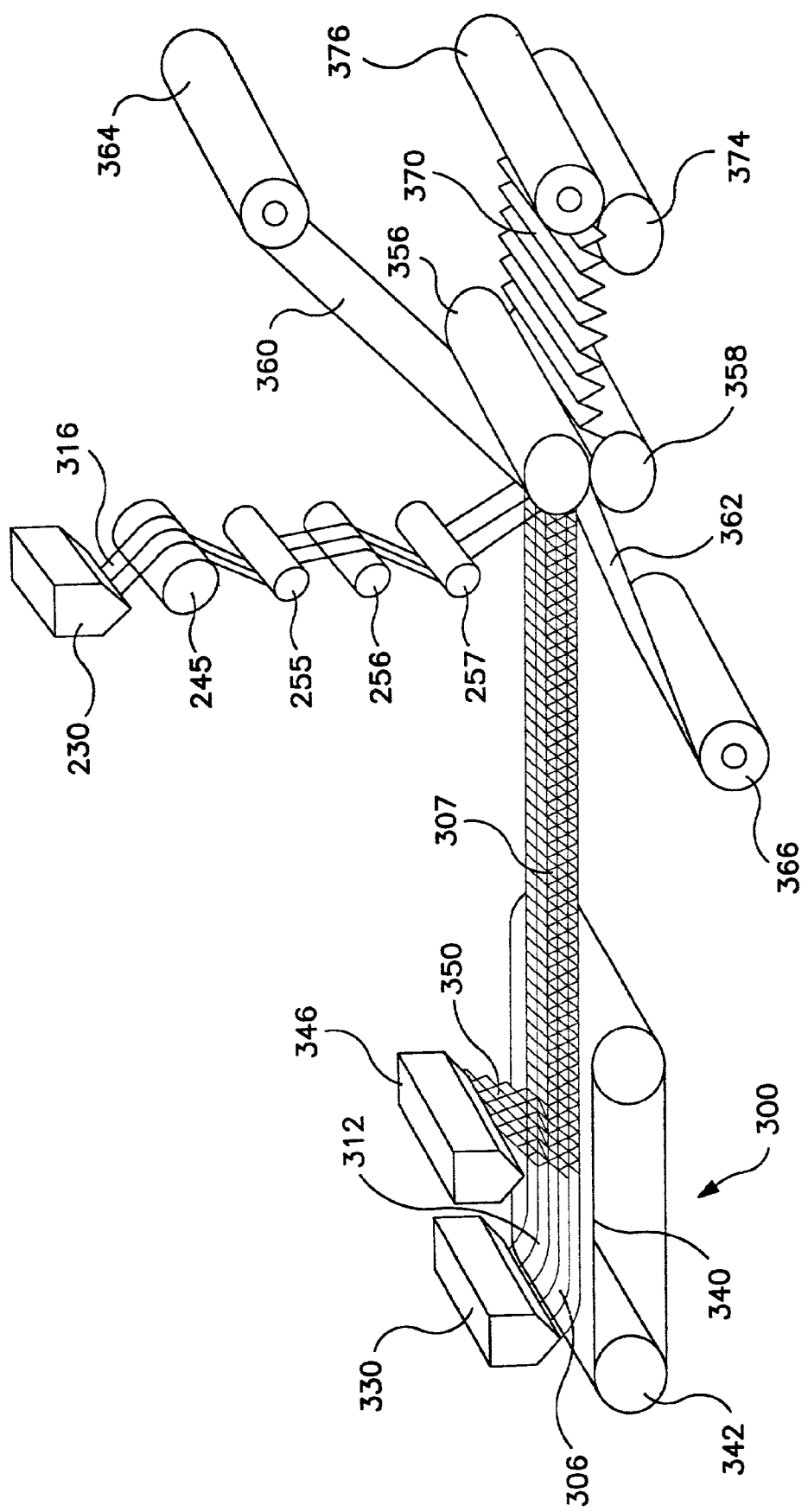

FIG. 12 illustrates a hybrid 300 of a CF SBL process and a VF SBL process for making a stretch-bonded TEL 370. A first extrusion apparatus 330 is fed with an elastic polymer or polymer blend from one or more sources (not shown). Extrusion apparatus 330 may be any of the various devices described with respect to FIG. 11. Apparatus 330 can be a meltblowing spinnerette operating without the heated gas (e.g., air) stream which flows past the die tip in conventional meltblowing processes. Apparatus 330 extrudes lower tension filaments 312 directly onto a conveyor system, which can be a forming wire system 340 (i.e., a foraminous belt) moving clockwise about rollers 342. Filaments 312 may be cooled using vacuum suction applied through the forming wire system, and/or cooling fans (not shown). The vacuum may also help hold the filaments against the forming wire system.

A meltblowing extruder 346 is used to add a reinforcing elastic meltblown layer 350 to the elastic filaments 312. Desirably, the meltblown layer 350 is made of the same elastic polymer as the low tension filaments 312. The resulting laminate 307 travels forward on the conveyor.

To make the higher tension region, a vertical filament die 230 extrudes higher tension (i.e., higher basis weight) elastic filaments 316 in a band which is narrower than the laminate 307 containing filaments 312. Filaments 316 pass around a chill roll 245, or a series of chill rolls, and a series of stretch rolls, for example two stretch rolls 255, 256, before being joined with laminate 307 between nip rolls 356 and 358, which are suitably smooth or patterned calender rolls. Simultaneously, facing layers 360 and 362 are unwound from supply rolls 364 and 366 and joined with the laminate between nip rolls 356 and 358 to make TEL 370. As TEL 370 is relaxed, it may assume the puckered configuration shown, due to retraction of high tension filaments 316 present in part of the laminate. TEL 370 may be flattened out between rolls 374 and 376, and wound onto roll 376.

To make the apparent elastic bands as shown in FIGS. 1 and 2, strips 125 of stretchable material (FIGS. 5-8) and/or colored bands, may be applied onto the TEL material, over the high tension regions, at any stage before, during or after manufacture of the TEL, using application and bonding techniques as described above. Strips 125 may be any extendible but inelastic material, and may be constructed from a spunbond web, meltblown web, carded (thermally bonded or hydraulically entangled) web, air laid web, film, paper, or the like. Except for paper, the foregoing strip materials may be formed from one or more thermoplastic polymers, such as a polyolefin such as polyethylene or polypropylene. The material used to make strips 125 may be a stretchable material. Alternatively, the material may be non-stretchable but capable of gathering along with the facing layer(s) as shown in FIG. 11. For instance, the strips 125 may be crimped or creped using known processes. The term "extendible" includes both stretchable and gatherable inelastic materials. In essence, any colored band, and/or any layer of material which gives the visual perception that an elastic band is present, may be added to the underlying targeted elastic material to create the apparent elastic bands. The apparent elastic bands may each have a width of about 0.1-2.5 inch, suitably about 0.25-1.5 inch, desirably about 0.5-1.0 inch.

Materials having apparent elastic bands, made according to the above-described embodiments of this invention can be employed in a wide variety of personal care absorbent articles including, for instance, diapers, training pants, swim wear, absorbent underpants, adult incontinence products, feminine hygiene products, and medical absorbent garments. The materials having apparent elastic bands are especially useful in absorbent articles requiring elastic in the waist and/or leg regions of a wearer. Materials having apparent elastic bands can also be used in protective garments requiring different levels of tension within an elastic region.

While the embodiments of the invention described herein are presently preferred, various modifications and improvements can be made without departing from the spirit and scope of the invention. The scope of the invention is indicated in the appended claims, and all changes that fall within the meaning and range of equivalents are intended to be embraced therein.

What is claimed is:

1. A disposable garment, comprising:
a chassis defining a waist opening and two leg openings; and
an apparent elastic band in the vicinity of at least one of the waist and leg openings, the apparent elastic band including a color pigment applied to a zone in a targeted elastic material that creates a visible perception of a discrete elastic band on the targeted elastic material where no actual elastic band is present on the targeted elastic material.

2. The disposable garment of claim 1, comprising the apparent elastic band in the vicinity of the waist opening.

3. The disposable garment of claim 1, comprising apparent elastic bands in the vicinity of both leg openings.

4. The disposable garment of claim 1, comprising apparent elastic bands in the vicinity of the waist and leg openings.

5. The disposable garment of claim 1, wherein the apparent elastic band comprises a high tension zone of the targeted elastic material, and a strip of extendible inelastic material over the high tension zone.

6. The disposable garment of claim 5, wherein the extendible inelastic material comprises a spunbond web.

7. The disposable garment of claim 6, wherein the spunbond web comprises a neck-stretched spunbond web.

8. The disposable garment of claim 5, wherein the extendible inelastic material comprises a meltblown web.

9. The disposable garment of claim 5, wherein the extendible inelastic material comprises a carded web selected from bonded carded webs and hydraulically entangled webs.

10. The disposable garment of claim 5, wherein the extendible inelastic material comprises an air laid web.

11. The disposable garment of claim 5, wherein the extendible inelastic material comprises a polymer film.

12. The disposable garment of claim 5, wherein the strip of extendible inelastic material further comprises a color pigment.

13. The disposable garment of claim 1, wherein the apparent elastic band comprises a high tension zone of the targeted elastic material, and a band of color pigment in or over the high tension zone.

14. A disposable absorbent garment, comprising:
a chassis including an absorbent composite structure and side panels extending from the absorbent composite structure;
waist and leg openings defined by the chassis; and
an apparent elastic band in the vicinity of at least one of the waist and leg openings, the apparent elastic band including a color pigment applied to a zone in a targeted elastic material that creates a visible perception of a discrete elastic band on the targeted elastic material where no actual elastic band is present on the targeted elastic material.

15. The disposable absorbent garment of claim 14, comprising the apparent elastic band in the vicinity of the waist opening.

16. The disposable absorbent garment of claim 14, comprising apparent elastic bands in the vicinity of the leg openings.

17. The disposable absorbent garment of claim 14, comprising apparent elastic bands in the vicinity of the waist and leg openings.

18. The disposable absorbent garment of claim 14, comprising apparent elastic bands in the side panels, further comprising at least one elastic band on the chassis substantially aligned with an apparent elastic band.

19. The disposable absorbent garment of claim 14, wherein the side panels comprise the targeted elastic material, the targeted elastic material having high and low tension zones.

20. The disposable absorbent garment of claim 19, wherein the targeted elastic material comprises a targeted elastic laminate.

21. The disposable absorbent garment of claim 20, wherein the apparent elastic band comprises a high tension zone of the targeted elastic laminate, and a strip of extendible inelastic material over the high tension zone.

22. The disposable absorbent garment of claim 21, wherein the extendible inelastic material comprises a nonwoven web.

23. The disposable absorbent garment of claim 22, wherein the nonwoven web comprises a neck-stretched nonwoven web.

24. The disposable absorbent garment of claim 21, wherein the strip of extendible inelastic material further comprises a color pigment.

25. The disposable absorbent garment of claim 20, wherein the apparent elastic band comprises a high tension zone of the targeted elastic laminate, and a band of color pigment in or over the high tension zone.

26. A disposable garment, comprising:
a chassis defining one or more openings; and
an apparent elastic band in the vicinity of at least one of the openings, the apparent elastic band including a color pigment applied to a zone in a targeted elastic material that creates a visible perception of a discrete elastic band on the targeted elastic material where no actual elastic band is present on the targeted elastic material.

27. The disposable garment of claim 26, comprising a diaper.

28. The disposable garment of claim 26, comprising a training pant.

29. The disposable garment of claim 26, comprising a feminine hygiene article.

30. The disposable garment of claim 26, comprising swim wear.

31. The disposable garment of claim 26, comprising an absorbent underpant.

32. The disposable garment of claim 26, comprising a protective gown.

33. The disposable garment of claim 26, comprising a protective cap.

34. The disposable garment of claim 26, comprising a protective glove.

35. The disposable garment of claim 26, comprising a protective drape.

36. The disposable garment of claim 26, comprising a protective face mask.

* * * * *